United States Patent [19]

Neuenschwander et al.

[11] Patent Number: 5,494,918
[45] Date of Patent: Feb. 27, 1996

[54] MULTICYCLIC TERTIARY AMINE POLYAROMATIC SQUALENE SYNTASE INHIBITORS

[75] Inventors: Kent Neuenschwander, Schwenksville; Dilip Amin, North Wales; Anthony C. Scotese, King of Prussia; Robert L. Morris, Wayne, all of Pa.

[73] Assignee: Rhone-Poulenc Rorer Pharmaceuticals Inc., Collegesville, Pa.

[21] Appl. No.: 320,075

[22] Filed: Oct. 7, 1994

Related U.S. Application Data

[60] Division of Ser. No. 959,898, Oct. 13, 1992, Pat. No. 5,385,912, which is a continuation-in-part of Ser. No. 667,686, Mar. 8, 1991, abandoned.

[51] Int. Cl.$^6$ ............... A61K 31/435; C07D 453/02
[52] U.S. Cl. ............. 514/305; 546/133; 546/137
[58] Field of Search ............... 546/133, 137; 514/305

[56] References Cited

U.S. PATENT DOCUMENTS

| | | | |
|---|---|---|---|
| 4,203,989 | 5/1980 | Yen et al. | 546/133 |
| 4,350,518 | 9/1982 | Sauter et al. | 546/133 |
| 4,355,166 | 10/1982 | Reiner | 546/137 |
| 4,631,287 | 12/1986 | Chakraborty et al. | 514/307 |
| 4,826,838 | 5/1989 | Richardson et al. | 14/210 |
| 4,839,369 | 6/1989 | Youssefyeh et al. | 14/314 |
| 4,861,897 | 8/1989 | Press | 548/217 |

FOREIGN PATENT DOCUMENTS

| | | |
|---|---|---|
| 2104981 | 3/1994 | Canada . |
| 0206751 | 12/1986 | European Pat. Off. . |
| 0219308 | 4/1987 | European Pat. Off. . |
| 9414803 | 7/1994 | WIPO . |

OTHER PUBLICATIONS

Poulter, C. D., et al., "Squalene Synthetase. Inhibition by an Ammonium Analogue of a Carbocationic Intermediate in the Conversion of Presqualene Pyrophosphate to Squalene," *J. Am. Chem. Soc.*, vol. 104, No. 25, pp. 7376–7378 (1982).

Poulter, C. D., et al., "Squalene Synthetase. Inhibition by Ammonium Analogues of Carbocationic Intermediates in the Conversion of Presqualene Diphosphate to Squalene," *J. Am. Chem. Soc.*, vol. III, No. 10, pp. 3734–3739 (1989).

Biller, S. A., et al., "Isoprenoid (Phosphenylmethyl)–phosphonates as Inhibitors of Squalene Synthetase," *J. Med. Chem.*, vol. 31, No. 10, pp. 1869–1871 (1988).

*Primary Examiner*—C. Warren Ivy
*Assistant Examiner*—Evelyn Huang
*Attorney, Agent, or Firm*—James A. Nicholson; Martin F. Savitzky; Raymond S. Parker, III

[57] ABSTRACT

This invention relates to polycyclic compounds containing two mono- and/or bicyclic rings and a basic tertiary amino group capable of forming an ammonium ion at biological pH and which reduces levels of serum cholesterol in the body without significantly reducing mevalonic metabolite synthesis. This invention relates also to pharmacological compositions and method of treatment for lowering serum cholesterol levels using the compounds of this invention.

11 Claims, 1 Drawing Sheet

MULTICYCLIC TERTIARY AMINE POLYAROMATIC SQUALENE SYNTASE INHIBITORS

BACKGROUND OF THE INVENTION

This is a divisional of application Ser. No. 07/959,898 filed Oct. 13, 1992 now U.S. Pat. No. 5,385,912 which is a continuation-in-part application of U.S. patent application Ser. No. 07/667,686, now abandoned, filed Mar. 8, 1991 and a continuation-in-part application of PCT Application having Serial Number PCT/US92/01773, filed Mar. 3, 1992.

FIELD OF THE INVENTION

The present invention relates to a class of novel compounds useful in the treatment of diseases associated with undesirable cholesterol levels in the body, and particularly diseases of the cardiovascular system, such as atherosclerosis.

Only about 7% of the total body cholesterol circulates in the plasma, where it has been linked to atherosclerosis. The remaining 93% is located in cells, where it performs vital structural and metabolic functions. Excluding the diet, which accounts for approximately one-third of the total body cholesterol, the cells obtain the necessary cholesterol by endogenous biosynthesis (scheme 1) or by removing low density lipoprotein (LDL) from the bloodstream. Approaches to the control of plasma cholesterol levels have been varied, however it has been shown that inhibiting endogenous cholesterol biosynthesis forces the cell to rely more on LDL uptake to satisfy their cholesterol requirements. Increased LDL uptake by cells, especially liver cells, has been shown to lower plasma cholesterol levels.

Squalene synthase is a microsomal enzyme that catalyzes the reductive dimerization of two molecules of farnesyl diphosphate to form squalene. While farnesyl diphosphate serves as the precursor to several other biologically important compounds, squalene is utilized only for cholesterol biosynthesis. Consequently, this is the first totally committed step in the biosynthesis of cholesterol (see scheme 1). Inhibition at this step would stop only de novo cholesterol synthesis while allowing other essential pathways to isopentenyl tRNA, the prenylated proteins, ubiquinone, and dolichol to proceed unimpeded.

Inhibition of HMG-CoA reductase, an enzyme positioned early in the cholesterol biosynthetic pathway, results in a decrease of de novo cholesterol biosynthesis and an accompanying up-regulation of LDL receptors. However due to a large induction in the amount of the HMG-CoA reductase enzyme, the effect of this inhibition is blunted somewhat and the maximum LDL cholesterol reductions attainable are limited. Since inhibition of squalene synthase does not cause the same amount of enzyme induction (HMG-CoA reductase or squalene synthase), it causes in a greater reduction of de novo cholesterol biosynthesis. This translates into more up-regulation of LDL receptors than is seen with an HMG-CoA reductase inhibitor and greater efficacy for lowering circulating LDL levels.

REPORTED DEVELOPMENTS

The literature describes the cholesterol biosynthetic pathway and possible means for the inhibition of squalene syntase. In a series of papers including *J. Am. Chem. Soc.*, 1982, 104, 7376–7378 and *J. Am. Chem. Soc.*, 1989, 111, 3734–3739, C. Dale Poulter, et al disclose that ammonium substituted cyclopropyl polyene compounds mimic the topological and electrostatic properties of the primary cation and tertiary cation of presqualene diphosphate. and in the presence of phosphate buffer, inhibit squalene syntase. Scott A. Biller et al in *J. Med. Chem.*, 1988, 31, 1869–1871 disclose that a series of stable, non-ionizable analogues of farnesyl diphosphate, comprising phosphomethylene phosphate polyene compounds, inhibit squalene syntase.

U.S. Pat. No. 4,839,369 discloses chemical compounds, having two aryl rings attached through a chain which may contain one to several atoms in length, and to which is attached to one of the aryl rings an acidic function such as azacyclic group, carboxlic acid or tetrazole group,are lipoxygenase inhibitors and possess anti-inflammatory and anti-allergic properties. Similar compounds are disclosed in U.S. Pat. No. 4,631,287, EP 0206751, and EP 0219308. None of these references disclose that any of the aforesaid acidic azacyclic compounds exhibit cholesterol reducing properties.

The present invention is directed to a class of novel tertiary amino polycyclic compounds which exhibit squalene syntase inhibition properties.

SUMMARY OF THE INVENTION

This invention comprises polycyclic compounds containing two mono- and/or bicyclic rings and a basic tertiary amino group. Preferred polycyclic compounds contain a tertiary amino group capable of forming an ammonium ion at biological pH. The compounds of this invention possess properties which reduce levels of serum cholesterol in the body without significantly reducing mevalonic metabolite synthesis and thus provide a therapeutic agent having fewer side effects than agents which act by inhibiting the HMG-CoA reductase enzyme. This invention relates also to pharmacological compositions and method of treatment for lowering serum cholesterol levels using the compounds of this invention.

DETAILED DESCRIPTION AND PREFERRED EMBODIMENTS

Figure 1:
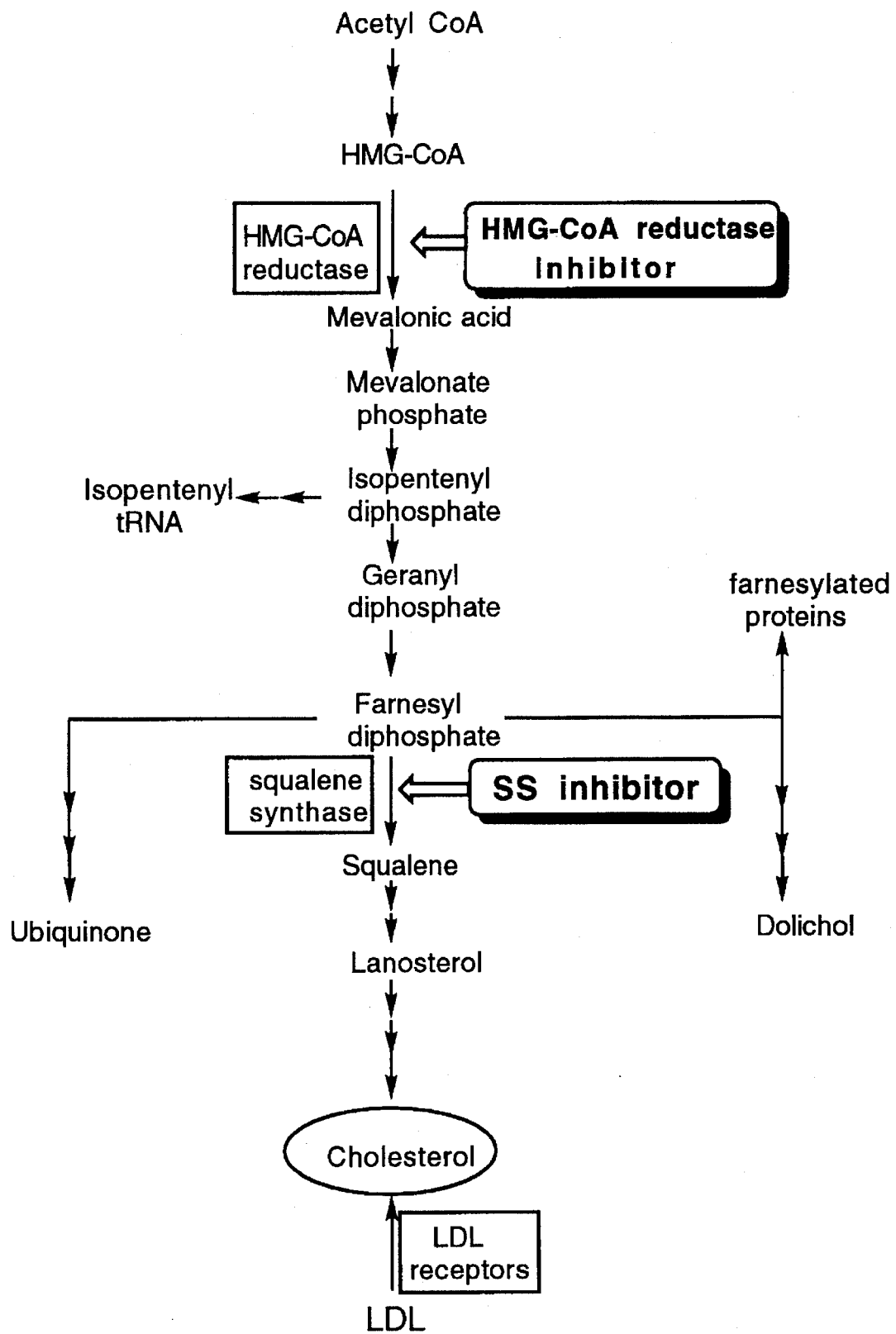
FIG. 1 is a schematic diagram of the biosynthetic pathway of cholesterol.

The compounds of the present invention comprise polycyclic ring compounds containing two mono- and/or bicyclic aryl and/or carbocyclic and/or heterocyclic rings and a tertiary cyclic amino group.

More specifically, the polycyclic tertiary amino compounds are described by Formula I:

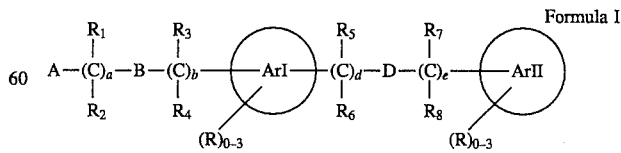

where:

Ar I and Ar II are independently a substituted or unsubstituted mono-, bi- or tricyclic ring;

A is preferably selected from the group consisting of be located at any appropriate position of the ring system and are described by the R definition above.

Preferred monocyclic rings include aryl and unsaturated carbocyclic and heterocyclic rings. Exemplary rings are substituted or unsubstituted pyrrole, thiophene, furan, cyclopentadiene, imidazole, pyrazole, 1,2,4-triazole, pyridine, pyrazine, pyrimidine, pyridazine, thiazole, isothiazole, oxazole, isoxazole, s-triazine and benzene.

Preferred bicyclic ring systems include bicyclic aryl and bicyclic unsaturated carbocyclic and heterocyclic rings. Exemplary bicyclic rings include substituted and unsubstituted indene, isoindene, benzofuran, dihydrobenzofuran, benzothiophene, indole, 1H-indazole, indoline, imadazole, azulene, tetrahydroazulene, benzofuran, benzothiaphene, benzopyrazole, benzoimadazole, benzoxazole, benzothiazole, 1,3-benzodioxole, 1,4-benzodioxan, purine, naphthalene, tetralin, coumarin, chromone, chromene, 1,2-dihydrobenzothiopyran, tetrahydrobenzothiopyran, quinoline, isoquinoline, quinazoline, pyrido[3,4-b]-pyridine, and 1,4-benzisoxazine.

Preferred tricyclic ring systems include tricyclic aryl and tricyclic unsaturated carbocyclic and heterocyclic rings. Exemplary tricyclic rings include substituted and unsubstituted phenanthrene, anthracene, acenaphthylene, perimidine, phenothiazine and phenoxazine.

The tertiary amino groups described by A are preferably the following:

As employed above and throughout this disclosure, the following terms, unless otherwise indicated, shall be understood to have the following meanings:

"Biological pH" refers to that pH of blood, plasma or serum in the body between about 7.2 and about 7.5 and which does not interfere with normal degradation of materials present therein. The normal pH of blood, plasma or serum values is about 7.35–7.45 and is preferably about pH 7.39–7.41.

"Monocyclic aryl" means a carbocyclic and/or heterocyclic aromatic ring. Preferred groups include phenyl, thienyl, pyridinyl, furyl and pyrimidinyl.

"Bicyclic aryl" means a bicyclic ring system composed of two fused carbocyclic and/or heterocyclic aromatic rings. Preferred groups include naphthyl, indolyl, benzothienyl, benzofuranyl, quinolinyl, chromonyl and purinyl.

"Tricyclic aryl" means a tricyclic ring system composed of three fused carbocyclic and/or heterocyclic aromatic rings. Preferred groups include acenaphthylene, phenanthrene, phenothiazine and phenoxazine.

"Aryl" means a carbocyclic or heterocyclic aromatic ring.

"Alkyl", either alone or with various substituents defined herein, means a saturated aliphatic hydrocarbon, either branched- or straight-chained. Preferred alkyl is "lower-alkyl" having about 1 to about 6 carbon atoms. Examples of alkyl include methyl, ethyl, n-propyl, isopropyl, butyl, sec-butyl, t-butyl, amyl and hexyl.

"Alkoxy" refers to an alkyl-O-group.

"Alkenyl" refers to a hydrocarbon having m least one point of unsaturation and may be branched- or straightwhere Y is NR', O, or S, Z is NR', O, S or a bond and m is 1–2;

B is CR'R', O, S, NR', SO, SO$_2$, NR'—C=O, O=C—NR', O=C, R'C=CR', C≡C or a bond;

D is CR'R', O, S, NR', SO, SO$_2$, NR'—C=O, O=C—NR', O=C, O—C=O, O=C—O, O=C—C=O, O=C—CH=CH, R'C=CR', C≡C, C=CHR', C=S, C=NOH or a bond;

R$_1$, R$_2$, R$_3$, R$_4$, R$_5$, R$_6$, R$_7$ and R$_8$ are independently hydrogen or (CH$_2$)$_x$—X where x is 0–5 and X is hydrogen, alkyl, alkenyl, aralkyl, hydroxy, alkoxy, aryloxy, aralkoxy, acyloxy, aryl, halo, amino, mono- and di-alkylamino or acylamino;

R$_1$ and R$_3$, together and/or R$_5$ and R$_7$ together may be (CH$_2$)$_n$ where n is 1–4:

geminal R$_1$ and R$_2$, R$_3$ and R$_4$, R$_5$ and R$_6$ or R$_7$ and R$_8$ groups may be (CH$_2$)$_p$ where p is 2–5;

R' is hydrogen, alkyl or aralkyl;

R is hydrogen, alkyl, aralkyl, hydroxy, alkoxy, aralkoxy, acyloxy, halo, haloalkyl, amino, mono- and di-alkylamino or acylamino; and a, b, d and e are 0–4; or a pharmaceutically acceptable salt thereof.

Preferably, Ar I and Ar II are independently a substituted or unsubstituted mono-, bi- or tricyclic system of about 5 to about 14 atoms which may be partially or completely unsaturated carbocyclic or heterocyclic and where each ring of said system contains 0 to about 2 hetero atoms selected from N, O and S provided said hetero atoms are not vicinal oxygen and/or sulfur atoms and where the substituents may chained. Preferred alkenyl groups have 2 to about 6 carbon atoms. Exemplary alkenyl groups include vinyl, allyl, ethynyl and isopropenyl.

The preferred aryloxy group is phenoxy.

"Aralkyl" means an alkyl group substituted by an aryl radical. The preferred aralkyl groups are benzyl or phenethyl.

The preferred aryloxy group is phenoxy.

The preferred aralkoxy groups are benzyloxy and phenethoxy.

The preferred acyloxy group is acetoxy.

"Halo" means a halogen. Preferred halogens include chloride, bromide and fluoride. The preferred haloalkyl group is trifluoromethyl.

The more preferred compounds of this invention include those compounds of Formula I where:

Ar I is phenyl or naphthyl;

Ar II is phenyl, thienyl, naphthyl, benzoxazolyl, benzothiazolyl, benzothienyl, benzodioxanyl, benzodihydrofuranyl, benzofuranyl, benzoxazolyl, 1,3-benzodioxolyl, 1,4-benzodioxanyl, quinolinyl, indolyl, acenaphthyl or dihydroacenaphthyl;

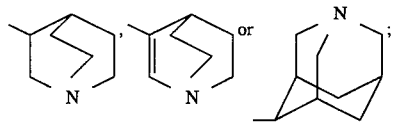

A is

B is CR'R', O, S, NR or a bond;

D is CR'R, O, S, NR', NR'—C=O, O=C—NR', O—C=O, O=C, R'C=CR', C≡C, C=CHR', C=S, C=NOH or a bond;

$R_1$, $R_2$, $R_3$, $R_4$, $R_5$, $R_6$, $R_7$ and $R_8$ are independently hydrogen or $(CH_2)_x$—X where x is 0–5 and X is hydrogen, alkyl, hydroxy, alkoxy, aryloxy, aralkoxy, or aryl;

$R_1$ and $R_3$ together and/or $R_5$ and $R_7$ together may be $(CH_2)n$ where n is 1–4:

geminal $R_1$ and $R_2$, $R_3$ and $R_4$, $R_5$ and $R_6$ or $R_7$ and $R_8$ groups may be $(CH_2)p$ where p is 2–5;

R' is hydrogen, alkyl or aralkyl;

R is hydrogen, alkyl, hydroxy, alkoxy, halo or haloalkyl; and a, b, d and e are 0–4.

The tertiary amino A group is most preferably one of the following:

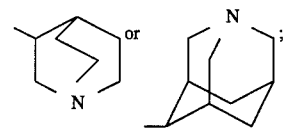

The most preferred compounds are described by Formula I where:

Ar I is phenyl or naphthyl;

Ar II is phenyl, thienyl, naphthyl, benzoxazolyl, benzothiazolyl, benzothienyl, benzodioxanyl, benzodihydrofuranyl, benzofuranyl, benzoxazolyl, 1,3-benzodioxolyl, 1,4-benzodioxanyl, quinolinyl, indolyl, acenaphthyl or dihydroacenaphthyl;

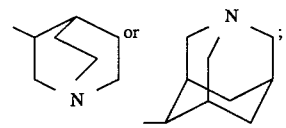

A is

B is CR'R', O or a bond;

D is CR'R, O=C, R'C=CR', C≡C, C=CHR' or a bond;

$R_1$, $R_2$, $R_3$, $R_4$, $R_5$, $R_6$, $R_7$ and $R_8$ are independently hydrogen or $(CH_2)_x$—X where x is 0–3 and X is hydrogen, alkyl, hydroxy or phenyl;

R' is hydrogen or loweralkyl;

R is hydrogen, loweralkyl, hydroxy, loweralkoxy, halo or trifluoromethyl; and a, b, d and e are 0–4.

A special embodiment of the compounds of this invention is described by Formulae II–IV.

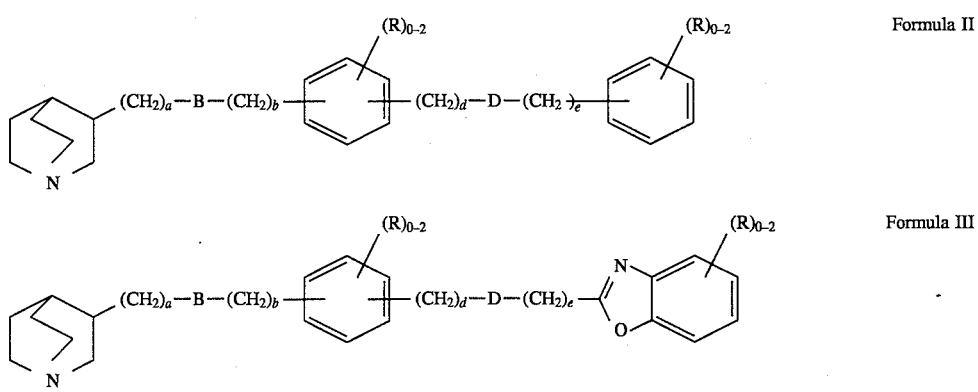

Formula II

Formula III

-continued

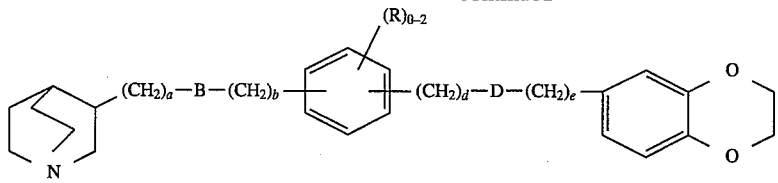

Formula IV where
- B is CR'R', O or a bond;
- D is CR'R', O=C, R'C=CR', C≡C, C=CHR' or a bond;
- R is hydrogen, loweralkyl, hydroxy, loweralkoxy, halo or trifluoromethyl; and a, b, d and e are 0–4.

The compounds of this invention may be prepared by employing procedures known in the literature starting from known compounds or readily preparable intermediates Exemplary general procedures follow. Since the compounds of this invention have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to the skilled artisan. This would further be dependent on the ring involved.

It is convenient to synthesize these molecules by employing condensation reactions at the above-described reactive B and D sites of the molecule. Exemplary general procedures are shown below and, for convenience, describe the benzene and quinuclidine ring system. Of course, while the following reactions involved are basic to developing substituted phenyl-quinuclidine molecules having desirable substituent groups present, the substitution pattern for other mono- or bicyclic rings depends on the chemistry of the particular ring. Any such adjustments to the chemistry would be familiar to one skilled in the art. Thus, in order to prepare those compounds where B or D is O, S or NR' the following reactions or combination of reactions are employed:

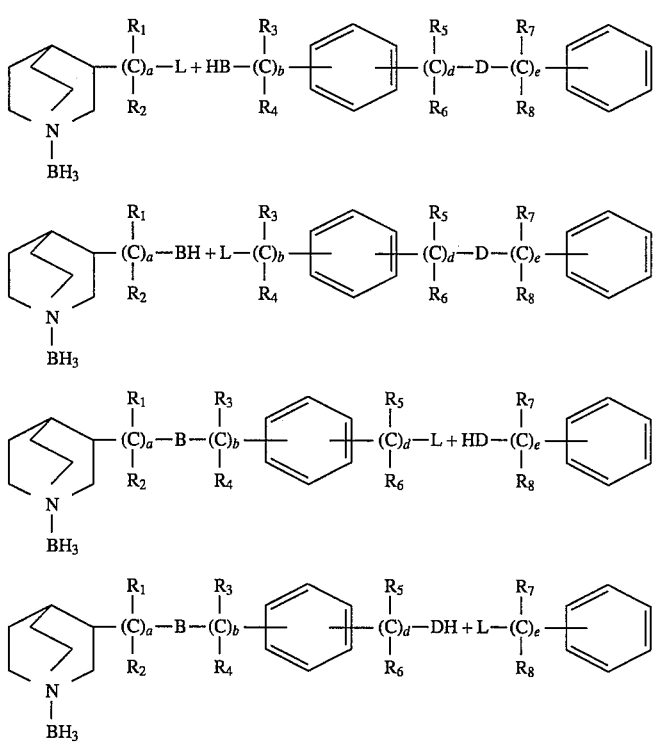

where L is a leaving group, preferably halo, tosylate or mesylate.

The cyclic amine is protected with the usual protecting groups such as hydroborane complex which is removed at the appropriate time with dilute acid such as HCl.

Where B and D are O or S, any base normally employed to deprotonate an alcohol or thiol may be used, such as sodium hydride, sodium hydroxide, triethyl amine, sodium bicarbonate, or diisopropylethylamine.

Reaction temperatures are in the range of −78° C. to reflux depending on the reactants involved. (Preferably 0° C. to room temperature). Reaction times vary from about 2 to about 96 hours. The reaction is usually carried out in a solvent that will dissolve both reactants and is inert to both as well. Solvents include, but are not limited to, diethyl ether, tetrahydrofuran, N,N-dimethyl formamide, dimethyl sulfoxide, dioxane and the like.

In the case where B or D is SO or $SO_2$, then treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating hydrogen peroxide, preferably about 30%, aqueous $H_2O_2$.

In certain of the following reaction schemes a metal salt may be used. Any appropriate metal salt such as Li, K, Na, Mg, Br or the like may be used.

Those compounds where D is —C═O are prepared by one of the following two reaction sequences, where in sequence 1, treatment of the substituted metal salt compound, such as the lithium, sodium potassium or Grignard compound, with an N-alkyl-N-alkoxybenzamide following the procedure of S. Nahm and S. M. Weinreb in Tet Letters, 22, 3815 (1981) results in the formation of the carbonyl chain.

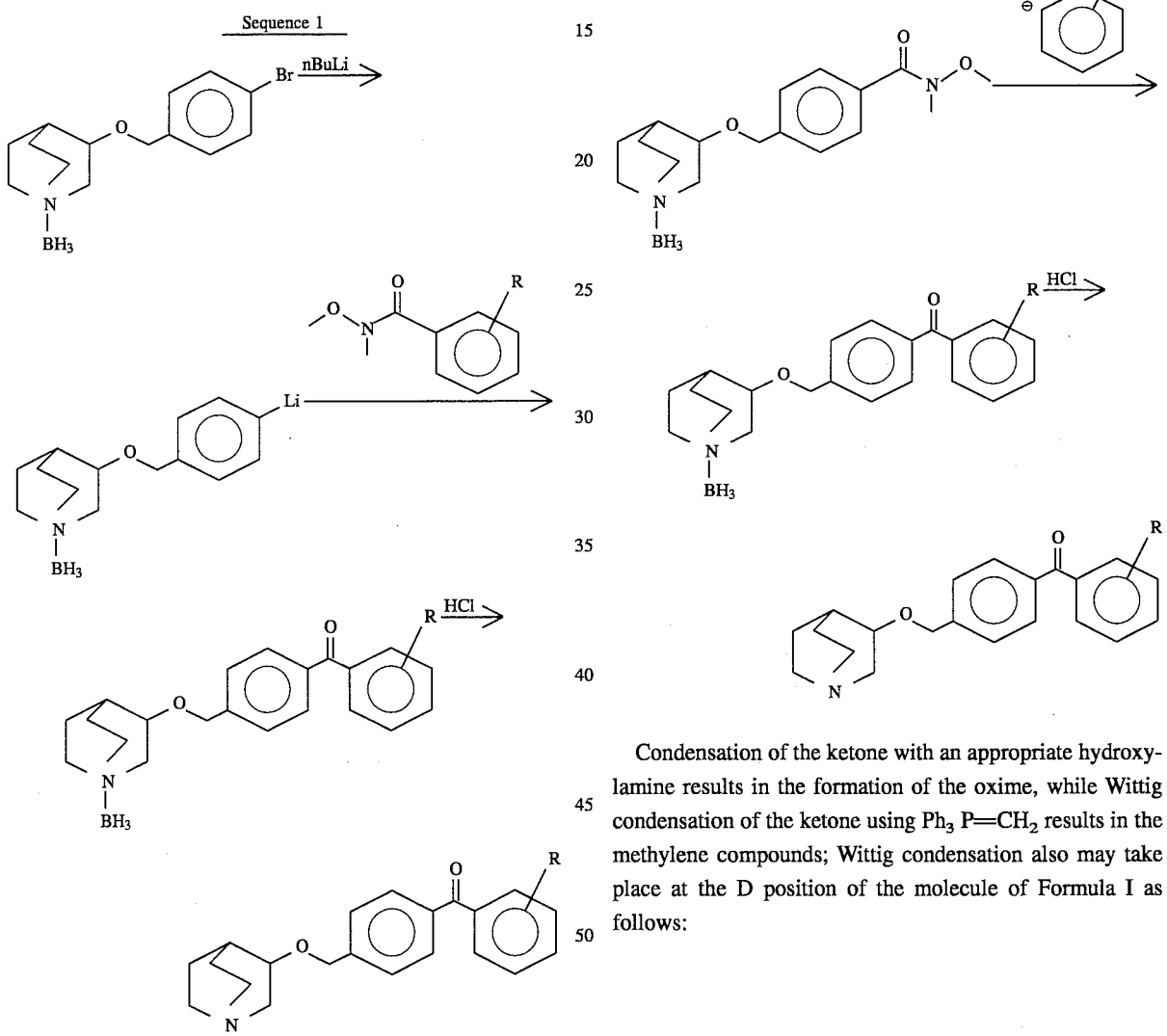

Condensation of the ketone with an appropriate hydroxylamine results in the formation of the oxime, while Wittig condensation of the ketone using $Ph_3 P\!=\!CH_2$ results in the methylene compounds; Wittig condensation also may take place at the D position of the molecule of Formula I as follows:

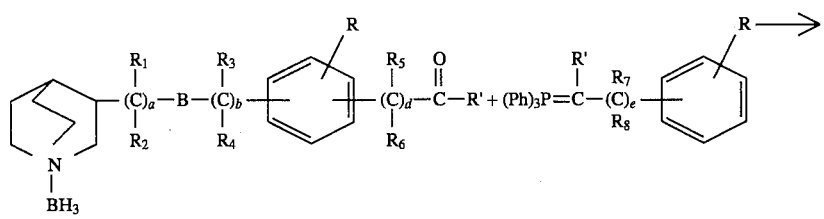

-continued

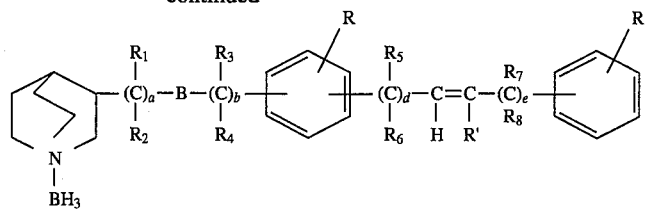

This may be carried out using normal Witting reaction conditions. When the appropriate aldehyde or ketone is reacted with a Wittig reagent then condensation results in formation of the double bond. This may then be reduced catalytically by known procedures such as Pd/C or any other suitable hydrogenating condition. The Wittig reagent is prepared by known art recognized procedures such as reaction of triphenylphosphine or diethylphosphone, with a substituted alkyl bromide followed by treatment with a strong organometallic or alkoxide base, such as n-BuLi or NaOH, results in the desired ylide. Of course this Witting condensation may also take place when the Wittig reagent is formed on the quinuclidine position of the molecule which is then condensed with the aldehyde from the Ar I portion.

Halogenation with $Br_2$ in $CCl_4$ on the double bond followed by double dehydration with $NaNH_2$ /liq $NH_3$ results in the triple bond compounds.

When B or D is —NR'—CO— or —CO—NR'— then condensation of the acid halide with the appropriate aniline will give the desired compound such as examples in the following schemes.

Sequence 3

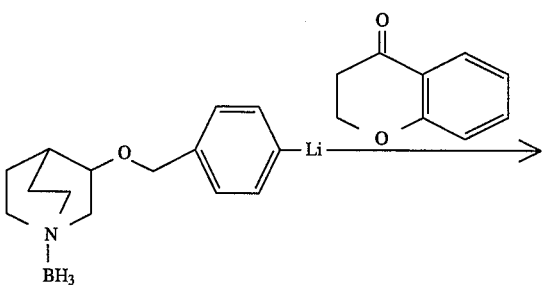

Condensation of the metal salt with a substituted phenylisocyanate results in the corresponding amide, as shown above. Reverse condensation will give the corresponding reverse amide.

Sequence 4

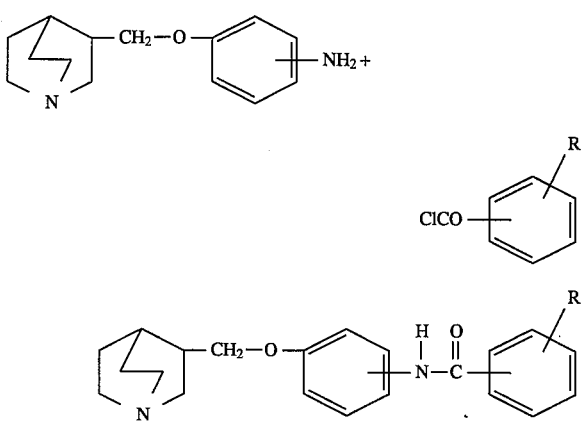

Condensation of the acid halide with the appropriate aniline will give the desired amide compound as shown in sequence 4.

Condensation of the metal salt with an aldehyde or ketone followed by dehydration results in the appropriate ring addition, as shown below.

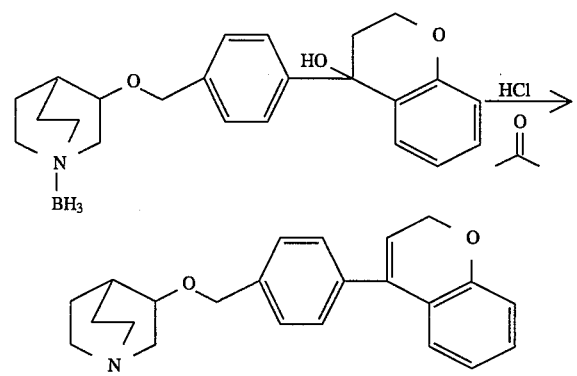

Certain compounds of this invention may have at least one asymmetric carbon atom such as those compounds having different geminal groups or those compounds which contain an asymmetric carbon atom. Further, certain compounds of this invention may exist in their cis or trans configuration such as those compounds where B or D is $CR_1=CR_1$. As a result, those compounds of this invention may be obtained either as racemic mixtures, diastereoisomeric mixtures or as individual enantiomers. When two or three asymmetric centers are present the product may exist as mixtures of two or four diastereomers. Of course it is understood that certain other compounds within the scope of this invention could have a number of stereocenters. In general, a compound with x stereocenters can have a maximum of $2^x$ stereoisomers. Therefore, a compound having three such centers gives rise to a maximum of eight stereoisomers, while one having four produces sixteen, etc. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity.

Reference to the separation of cis and trans isomers by chromatography may be found in W. K. Chan, et al, J. Am. Chem. Soc. 96, 3642, 1974.

It is to be understood that the scope of this invention encompasses not only the various isomers which may exist but also the various mixture of isomers which may be formed.

The resolution of the compounds of this invention and their starting materials may be carried out by known procedures. Incorporation by reference is hereby made to the four volume compendium *Optical Resolution Procedures for Chemical Compounds*: Optical Resolution Information Center, Manhattan College, Riverdale, N.Y. Such procedures are useful in the practice of this invention. A further useful reference is *Enantiomers, Racemates and Resolutions*: Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, maleic, tartaric and the like which are pharmaceutically acceptable. Basic salts for pharmaceutical use are the Na, K, Ca and Mg salts.

Various substituents on the present new compounds can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added by nitration and the nitro group converted to other groups, such as amino by reduction, and halo by diazotization of the amino group and replacement of the diazo group. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

The compounds of the present invention may be prepared by the following representative examples.

EXAMPLE 1

3-hydroxy-1-azabicyclo[2.2.2.]octane borane complex

To an ice cold suspension of 38 g (300 m mole) of 3-quinuclidinol in 200 ml of anhydrous THF is added 300 ml (300 m mole) of a 1M borane-THF complex dropwise over 1 hour. The mixture is stirred at room temperature for 1 hour, poured into 700 ml of water and extracted with 700 ml of chloroform (2x). The chloroform layers are combined, washed with brine, and dried over magnesium sulfate. The mixture is filtered and evaporated in vacuo. The residue is redissolved in 150 ml of ether and diluted with 1000 ml of petroleum ether and the resulting precipitate collected and vacuum dried to afford 3-hydroxy-1-azabicyclo[2.2.2.]octane borane complex, (m.p. 186°–8° C. dec.).

EXAMPLE 2

3-[(4-Bromophenyl)methoxy]-1-azabicyclo[2.2.2.] octane borane complex

To a suspension of 6.24 g (156 m mole) of 60% sodium hydride, in 70 ml of anhydrous DMF, is added a solution of 22 g(156 m mole) of 3-hydroxy-1-azabicyclo[2.2.2.]octane borane complex in 100 ml of anhydrous DMF dropwise over 35 minutes. The mixture is stirred at room temperature for 30 minutes and a solution of 29.0 g (156 m mole) of 4-bromobenzyl bromide in 50 ml of DMF added dropwise over 20 minutes. The mixture is stirred at room temperature for 18 hours and then diluted with water to the cloudy point. The precipitate which forms is collected and the filter cake washed with water. After drying, the filter cake is dissolved in 150 ml of warm ethyl acetate and the solution diluted with petroleum ether to give 3-[(4-Bromophenyl)methoxy]-1-azabicyclo[2.2.2.]octane borane complex, (m.p. 90°–3° C. dec.).

EXAMPLE 3

3-[4-(4-chlorobenzoyl)benzyloxy]-1-azabicyclo[2.2.2.] octane hydrochloride

To a solution of 9.0 g (29 m mole) of 3-[(4-bromophenyl)methoxy]-1-azabicyclo[2.2.2.] octane borane complex in 80 ml of anhydrous THF cooled to −78° C. is added 11.6 ml (29 m mole) of a 2.5M hexane solution of n-butyllithium dropwise over 5 minutes. The mixture is stirred at −78° C. for 25 minutes and a solution of 5.79 g (29 m mole) of 4-chloro-N-methyl-N-methoxybenzamide (S. Nahm and S. M. Weinreb, Tet. Letters, 22, 3815(1981)) in 50 ml of THF added dropwise over 5 minutes. The cooling bath is removed and the mixture stirred for 1 hour and then poured into 150 ml of water. The mixture is extracted with 200 ml of ether. The ether layer is washed with water and dried over magnesium sulfate and filtered. The filtrate is evaporated and the residue redissolved in acetone. The solution is diluted to the cloudy point with petroleum ether and the resulting precipitate collected to give a solid melting at 134°–6° C. This solid is suspended in 75 ml of acetone cooled in an ice bath and 15 ml of 3N HCl is added dropwise over 5 minutes. The cooling bath is removed and the mixture stirred at room temperature for 2.5 hours. The mixture is concentrated in vacuo and basified with sodium carbonate and partitioned between 50 ml of brine and 200 ml of chloroform. The chloroform layer is washed with brine and dried over magnesium sulfate and filtered. The filtrate is evaporated and the residue redissolved in ethanolic HCl. The solution is diluted with ether and the resulting precipitate collected and recrystallized from acetonitrile-ether to give 3-[4-(4-chlorobenzoyl)benzyloxy]-1-azabicyclo[2.2.2.]octane hydrochloride, (m.p. 186°–8° C. dec.)

EXAMPLE 4

3-[4-(2-fluoro-6.7-dihydro-5H-benzocycloheptene-9-yl)benzyloxy]-1-azabicyclo[2.2.2.]octane hydrochloride To a solution of 1.64 g (5.3 mole) of 3-[(4-bromophenyl)methoxy]-1-azabicyclo[2.2.2.]octane borane complex in 50 ml of anhydrous THF is added 2.12 ml (5.3 m mole) of a 2.5M hexane solution of n-butyllithium dropwise over 5 minutes at −78° C. The mixture is stirred at −78° C. for 30 minutes and a solution of 1.0 g (5.6 m mole) of 8-fluoro-1-benzosuberone in 20 ml of THF is added dropwise over 5 minutes. The mixture is stirred for 4 hours warming to room temperature. The mixture is poured into 50 ml of water and extracted with 100 ml of ether. The ether is washed with water and dried over magnesium sulfate and then filtered. The filtrate is evaporated and the residue purified by flash chromatography using 7:3 hexane:ethyl acetate on silica gel. The product residue is dissolved in 10 ml of acetone and 6 ml of 3N HCl is added. The mixture is then stirred at room temperature for 45 minutes and concentrated in a rotary evaporator. The residue is basified with sodium carbonate and partitioned between 15 ml of brine and 75 ml of chloroform. The chloroform layer is washed with brine and dried over magnesium sulfate then filtered. The filtrate is evaporated and the residue dissolved in ethanolic HCl. The solution is diluted with ether and the precipitate collected and recrystallized from acetone-petroleum ether to give 3-[4-(2-fluoro-6,7-dihydro-5H-benzocycloheptene-9-yl)benzyloxy]-1-azabicyclo[2.2.2.]octane hydrochloride, (m.p. 196°–8° C. dec.)

EXAMPLE 5

3-[2-(benzyl)benzyloxy]-1-azabicyclo[2.2.2.]octane hydrochloride

To a suspension of 0.56 g (13.9 m mole) of 60% sodium hydride in 25 ml of anhydrous DMF is added a solution of 1.96 g (13.9 m mole) of 3-hydroxy-1-azabicyclo[2.2.2.]octane borane complex in 25 ml of DMF dropwise over 5 minutes. The mixture is stirred at room temperature for 25 minutes and a solution of 4.0 g (15.3 m mole) of 2-benzylbenzyl bromide in 10 ml of DMF is added dropwise over 5 minutes. The mixture is stirred at room temperature for 4 hours and is poured into 150 ml of water and extracted with 100 ml of ether. The ether layer is worked up in the usual way to give 3-[2-(benzyl)benzyloxy]-1-azabicyclo [2.2.2.] octane hydrochloride, (m.p. 133°–5° C. dec.)

EXAMPLE 6

3-[4-(2-(phenyl)ethanyl)benzyloxy]-1-azabicyclo[2.2.2.]octane hydrochloride

To a suspension of 0.6 g (15 m mole) of 60% sodium hydride in 25 ml of anhydrous DMF is added a solution of 2.1 g (15 m mole) of 3-hydroxy-1-azabicyclo[2.2.2.]octane borane complex in 25 ml of DMF dropwise over 5 minutes. The mixture is stirred at room temperature for 30 minutes and a solution of 4.6 g (16.7 m mole) of 1-(4-bromomethyl)phenyl-2-phenylethane in 15 ml of DMF is added dropwise over 5 minutes. The mixture is stirred at room temperature for 16 hours and is poured into 150 ml of water. The mixture is extracted with 100 ml of ether. The ether is dried over magnesium sulfate and the evaporated residue is worked up in the usual way to give 3-[4-(2(Phenyl)ethanyl)benzyloxy]-1-azabicyclo[2.2.2.]octane hydrochloride, (m.p. 193°–5° C. dec.)

EXAMPLE 7

3-[4-(2-(phenyl)ethenyl)benzyloxy]-1-azabicyclo[2.2,2,]octane hydrochloride

To a suspension of 2.0 g (50 m mole) of 60% sodium hydride in 75 ml of anhydrous DMF is added a solution of 7.05 g (50 m mole) of 3-hydroxy-1-azabicyclo[2.2.2.]octane borane complex in 50 ml of DMF dropwise over 20 minutes. The mixture is stirred at room temperature for 45 minutes and a solution of 13.9 g (51 m mole) of 4-bromomethylstilbene (prepared from 4-stilbenemethanol and bromotrimethyl silane) in 75 ml of DMF is added dropwise over 25 minutes. The mixture is stirred at room temperature for 16 hours and poured into 350 ml of rapidly stirred water. The solid is collected, dried and recrystallized from THF-petroleum ether to give 8 g of material (−140°–3° C. mp.) This solid is suspended in 50 ml of acetone and 20 ml of 3N HCl added. The mixture is stirred at room temperature for 45 minutes and worked up in the usual way to give 3-[4-(2-(phenyl)ethenyl)benzyloxy]-1-azabicyclo[2.2.2.]octane hydrochloride, (234°–6° C. m.p.)

EXAMPLE 8

3-[4-(2-(phenyl)ethynyl)benzyloxy]-1-azabicyclo [2.2.2.]octane hydrochloride To a suspension of 66 mg (1.66 m mole) of 60% sodium hydride in 35 ml of anhydrous DMF is added a solution of 0.23 g (1.66 m mole) of 3-hydroxy-1-azabicyclo[2.2.2.]octane borane complex in 10 ml of DMF dropwise over 3 minutes. The mixture is stirred at room temperature for 30 minutes and a solution of 0.45 g (1.66 m mole) of (4-bromomethylphenylethynyl)phenyl (prepared by treating (4-phenylethynyl)benzaldehyde (H. A. Krick and F. R. Heck, J. Organomet. Chem., 93 (2), 259–63 (1975)) with sodium borohydride followed by bromotrimethylsilane) in 10 ml of DMF is added dropwise over 3 minutes. The mixture is stirred at room temperature for 4 hours and poured into 75 ml of water. The mixture is extracted with 100 ml of ether. The ether is dried and worked up in the usual way to give 3-[4-(2-(phenyl)ethynyl)-benzyloxy]-1-azabicyclo[2.2.2.]octane hydrochloride, (223°–5° C. m.p.)

EXAMPLE 9

3-(4-(N-phenylbenzamide)methyloxy)-1-azabicyclo [2.2,2,]octane hydrochloride To a solution of 3.0 g (9.68 m mole) of 3-(4-bromophenyl)methoxy-1-azabicyclo[2.2.2.]octane borane complex in 50 ml of anhydrous THF cooled to −78° C. is added 3.87 ml (9.68 m mole) of a 2.5M hexane solution of n-butyllithium (Aldrich) dropwise over 3 minutes. The mixture is stirred at −78° C. for 30 minutes and a solution of 1.3 g (11 m mole) of phenylisocyanate in 10 ml of THF is added dropwise over 5 minutes. The mixture is stirred for 4 hours warming to room temperature. The mixture is poured into 70 ml of water and is extracted with 100 ml of ether. The ether is dried over magnesium sulfate and the evaporated residue is worked up in the usual way. The hydrochloride salt is recrystallized from acetonitrile to afford 70 mg of 3-(4-(N-phenylbenzamide)methyloxy)-1-azabicyclo[2.2.2.]octane hydrochloride, (206°–8° C. dec.)

EXAMPLE 10

3-(4-(4-chloro-a-hydroxybenzyl)benzyloxy)-1-azabicyclo[2.2.2.]octane hydrochloride To a solution of 1.5 g (4.83 m mole) of 3-(4-bromophenyl)methoxy-1-azabicyclo[2.2.2.]octane borane complex in 35 ml of anhydrous THF cooled to −78° C. is added 1.93 ml (4.83 m mole) of a 2.5M hexane solution of n-butyllithium (Aldrich) dropwise over 3 minutes. The mixture is stirred at−78° C. for 30 minutes and a solution of 0.7 g (5.0 m mole) of 4-chlorobenzaldehyde (Aldrich) in 10 ml of THF added dropwise over 5 minutes. The mixture is stirred for 3 hours warming to room temperature. The mixture is poured into 75 ml of water and extracted with 100 ml of ether. The mixture is worked up in the usual way to give 3-(4-(4-chloro-a-hydroxybenzyl)benzyloxy)-1-azabicyclo[2.2.2.]octane hydrochloride, (70° C. dec. m.p.)

EXAMPLE 11

3-[4-(1-(4-chlorophenyl)ethenyl)benzyloxy]1-azabicyclo [2.2.2.]octane hydrochloride To a suspension of 0.34 g (8.5 m mole) of 60% sodium hydride in 35 ml of anhydrous DMF is added a solution of 1.2 g (8.5 m mole) of 3-hydroxy-1-azabicyclo[2.2.2.]octane borane complex in 15 ml of DMF dropwise over 5 minutes. The mixture is stirred at room temperature for 30 minutes and a solution of 2.7 g (8.78 m mole) of 1-(4-bromomethyl)phenyl-1-(4chlorophenyl)ethylene in 10 ml of DMF is added dropwise over 5 minutes. The mixture is stirred at room temperature for 3 hours and is poured into 100 ml of water and extracted with 100 ml of ether. The ether is dried over magnesium sulfate, filtered and evaporated. The residue is purified by flash chromatography on silica gel using 4:1 hexane:ethyl acetate as the eluent. The oil product is converted to its hydrochloride salt in the usual fashion to give 3-[4-(1-(4-chlorophenyl)ethenyl)benzyloxy]-1-azabicyclo[2.2.2.]octane hydrochloride, (163°–5° C. m.p.)

EXAMPLE 12

3-[4-(2H-1-benzopyran-4-yl)benzyloxy]-1-azabicyclo [2.2.2.]octane hydrochloride To a solution of 0.5g (1.6 m mole) of 3-(4-bromophenyl)methoxy-1-azabicyclo[2.2.2.]octane borane complex in 40 ml of anhydrous THF cooled to −78° C. is added 0.64 ml (1.6 m mole) of a 2.5M hexane solution of n-butyllithium (Aldrich) dropwise over 5 minutes. The mixture is stirred for 5 minutes and a solution of 0.26 g (1.8 m mole) of 4-chromanone (Aldrich) in 5 ml of THF is added dropwise over 5 minutes. The mixture is stirred for 1 hour warming to room temperature and poured into 75 ml of water. The mixture is extracted with 100 ml of ether, dried and evaporated to dryness and the residue worked up in the usual way to give 3-[4-(2H-1-benzopyran-4-yl)benzyloxy-1-azabicyclo [2.2.2.]octane hydrochloride, (178°–81° C. m.p.)

EXAMPLE 13

3-[4-(2H-1-benzothiopyran-4-yl)benzyloxy]-1-azabicyclo[2.2.2.]octane hydrochloride To a solution of 2.0 g (6.6 m mole) of 3-(4-bromophenyl)methoxy-1-azabicyclo[2.2.2.]octane borane complex in 40 ml of anhydrous THF cooled to −78° C. is added 2.64 ml (6.6 m mole) of a 2.5M hexane solution of n-butyllithium (Aldrich) dropwise over 3 minutes. The mixture is stirred at −78° C. for 30 minutes and a solution of 1.08 g (6.6 m mole) of thiochroman-4-one (Aldrich) in 10 ml of THF is added dropwise over 5 minutes. The solution is stirred for 4 hours warming to room temperature. The mixture is poured into 70 ml of water and extracted with 100 ml of ether. The ether is washed with water and dried over magnesium sulfate and filtered. The filtrate is evaporated and the residue redissolved in 15 ml of acetone and 7 ml of 3N HCl added. The mixture is stirred at room temperature for 24 hours. The mixture is concentrated in vacuo and basified with sodium carbonate. The mixture is partitioned between 15 ml of brine and 70 ml of chloroform. The chloroform is evaporated and the residue dissolved in ethanolic HCl and diluted with petroleum ether. The resulting precipitate is collected and recrystallized from ethanol to give 3-[4-(2H-1-benzothiopyran-4-yl)benzyloxy] -1-azabicyclo[2.2.2.]octane hydrochloride, ( 140° C. dec.)

When the above example is followed but the residue which results from the ether extract is allowed to stand in acetone and 3N HCl for less than 1 hour before workup, then the hydrated form results which may then be isolated.

EXAMPLE 14

3-[4-(6,7-dihydrothianaphthene-4-yl)benzyloxy]-1-azabicyclo[2.2.2.]octane hydrochloride To a solution of 1.95 g (6.3 m mole) of 3-(4-bromophenyl)methoxy-1-azabicyclo[2.2.2.]octane borane complex in 50 ml of anhydrous THF cooled to −78° C. is added 2.52 ml (6.3 m mole) of a 2.5M hexane solution of n-butyllithium (Aldrich) dropwise over 5 minutes. The mixture is stirred at −78° C. for 30 minutes and a solution of 1.0 g (6.57 m mole) of 4-keto-4,5,6,7-tetrahydrothianaphthene in 15 ml of THF is added dropwise over 5 minutes. The mixture is stirred for 4 hours warming to room temperature and poured into 100 ml of water. The mixture is extracted with 100 ml of ether and washed with water and dried over magnesium sulfate. The evaporated ether residue is purified by flash chromatography on silica gel using 7:3 hexane:ethyl acetate as the eluent. The product residue is dissolved in 10 ml of acetone and 6 ml of 3N HCl is added. The mixture is stirred at room temperature for 45 minutes and is basified and extracted into chloroform. The evaporated chloroform layer is dissolved in ethanolic HCl and the solution is diluted with petroleum ether. The resulting precipitate is collected and recrystallized from ethanol/petroleum ether to give 3-[4-(6,7-dihydrothianaphthene-4-yl)benzyloxy]-1-azabicyclo[2.2.2.]octane hydrochloride, (200°-3° C. dec.)

EXAMPLE 15

When 3-quinuclidinol in Example 1 is replaced by the amino of Table I below, then the corresponding products are obtained.

TABLE I 3-quinuclidinthiol
3-N-acetylaminoquinuclidine
3-hydroxymethylquinuclidine
2-hydroxymethylquinuclidine
5-hydroxy-3-acetyl-3,4,5,6-tetrahydropyrimidine
4-hydroxy-(1-azabicyclo[3.3.1.]nonane)
7-hydroxy-(3-oxo-9-methylazabicyclo[3.3.1.]nonane)
3-hydroxy-(9-methylazabicyclo[3.3.1.]nonane)
7-hydroxy-(3-methylazabicyclo[3.3.1.]nonane)
1-azatricyclo[3.3.1.1,3.7]decan-4-ol

EXAMPLE 16

When 4-bromobenzylbromide in Example 2 is replaced by the compounds of Table II below, then the corresponding products are prepared.

TABLE II 4-bromophenethylbromide
2-bromonaphth-1-ylmethylbromide
4-bromonaphth-1-ylmethylbromide
2-bromothien-5-ylmethylbromide
4-bromopyrid-2-ylmethylbromide
2-methyl-4-bromobenzylbromide
1-bromonaphth-2-ylmethylbromide
5-bromonaphth-1-ylmethylbromide
2-bromothien-4-ylmethylbromide
2-bromopyrid-6-ylmethylbromide
2-bromopyrid-5-ylmethylbromide

EXAMPLE 17

When 4-chloro-N-methyl-N-methoxybenzamide in Example 3 is replaced by the compounds of Table III below, then the corresponding products are obtained.

TABLE III

1-N-methyl-N-methoxynaphthamide
4-methoxy-N-methyl-N-methoxybenzamide
3-chloro-4-methyl-N-methyl-N-methoxybenzamide
2-fluoro-N-methyl-N-methoxybenzamide
3-fluoro-N-methyl-N-methoxybenzamide
4-fluoro-N-methyl-N-methoxybenzamide
4-methyl-N-methyl-N-methoxybenzamide
4-trifluoromethyl-N-methyl-N-methoxybenzamide
4-nitro-N-methyl-N-methoxybenzamide
2-N-methyl-N-methoxyquinolinamide
4-chloro-N-methyl-N-methoxyphenylacetamide

EXAMPLE 18

When 8-fluoro-1-benzosuberone in Example 4 is replaced by the compounds of Table IV below, then the corresponding products are obtained.

TABLE IV 1-benzosuberone
∝-tetralone
cyclohexanone
4-chromanone
thiochroman-4-one
pyran-4-one
2-cyclopenten-1-one
5,7-dimethyl-3,4-dihydronaphth-1-one
5-chloroindan-1-one
2,2-dimethyl-2H-1-benzopyran-4-one
5-methoxy-1-indanone
6,7-dihydro-5H-benzocyclohepten-9-one
3,3-dimethylindan-1-one

EXAMPLE 19

When 4-bromomethylstilbene in Example 7 is replaced with the compounds of Table V below, then the corresponding products are obtained.

TABLE V 4-biphenylmethyl bromide
2-biphenylmethyl bromide
2-biphenylmethyl bromide
4-(cyclohexen-1-yl)benzyl bromide
4-phenylmethoxybenzyl bromide
3-phenoxybenzyl bromide
3,4-dichlorophenoxybenzyl bromide
3-(4-t-butylphenoxy)benzyl bromide
4-(3,3,5,5-tetramethylcyclohexen-1-yl)benzyl bromide
4-(4,4,6,6-tetramethylcyclohexen-1-yl)benzyl bromide
4-(4,4-dimethylcyclohexen-1-yl)benzyl bromide
4-chlorobenzoylbenzyl bromide
4-(1-phenethenyl)benzyl bromide
4-(2-phenylethyl)benzyl bromide
2-benzylbenzyl bromide
3-benzyloxybenzyl bromide
2-phenethylbenzyl bromide
4-(2,5-dimethylstyryl)benzyl bromide
4-(3,4-dichlorostyryl)benzyl bromide
4-(4-fluorostyryl)benzyl bromide
4-phenoxybenzyl bromide
4-((1-benzoyl-1-methyl)ethyl)benzyl bromide
4-benzoylbenzyl bromide
N-methylbenzamidobenzyl bromide
4-phenylethynylbenzyl bromide
4-(1-(4-chlorophenyl)ethenyl)benzyl bromide
4-(1-(2-chlorophenyl)ethenyl)benzyl bromide
4-(4-methylphenylsulfonyl)benzyl bromide
3-benzoylbenzyl bromide
4-(benzoxazol-2-yl)benzyl bromide
4-(naphth-2-yl)benzyl bromide

EXAMPLE 20

3-(benzil-4-yl)methyloxy)-1-azabicyclo[2.2.2.]octane hydrochloride

To a suspension of 0.6 g (15 m mole) of 60% sodium hydride in 25 ml of anhydrous DMF is added a solution of 2.1 g (15 m mole) of 3-hydroxy-1-azabicyclo[2.2.2.]octane borane complex in 25 ml of DMF dropwise over 5 minutes. The mixture is stirred at room temperature for 30 minutes and a solution of 4.85 g (16.7 m mole) of 4-bromomethylbenzil (B. Krieg and G. Manecke, Ber., 101, 1480–84 (1963)) in 15 ml of DMF is added dropwise over 5 minutes. The mixture is stirred at room temperature for 16 hours and is poured into 150 ml of water. The mixture is extracted with 100 ml of ether. The ether is dried over magnesium su,fate and the evaporated residue is worked up in the usual way to give 3-(benzil-4-yl)methyloxy)-1-azabicyclo[2.2.2.]octane hydrochloride.

EXAMPLE 21

3-[4-(styrylcarbonyl)benzyloxy]-1-azabicyclo[2.2.2.] octane hydrochloride

To a solution of 1.5 g (4.84 m mole) of 3-(4-bromophenyl)methoxy-1-azabicyclo[2.2.2.]octane borane complex in 30 ml of anhydrous THF cooled to −78° C. is added 1.94 ml (4.84 m mole) of a 2.5M hexane solution of n-butyllithium (Aldrich) dropwise over 3 minutes. The mixture is stirred at −78° C. for 20 minutes and a solution of 0.93 g (4.84 m mole) of N-methoxy-N-methyl-3-(E)-phenyl-2-propenbenzamide (prepared from trans cinnamoyl chloride and N,O-dimethylhydroxylamine via the S. Nahm and S. M. Weinreb procedure, Tet. Letters, 22, 3815 (1981)) in 10 ml of THF is added dropwise over 5 minutes. The cooling bath is removed and the mixture is stirred for 1 hour and is poured into 70 ml of water. The mixture is extracted with 100 ml of ether. The ether layer is washed with water and is dried over magnesium sulfate and filtered. The filtrate is evaporated and the residue is redissolved in acetone. The solution is diluted to the cloudy point with petroleum ether and the resulting precipitate collected to give solid melting 135°–7° C. This solid is suspended in 10 ml of acetone and 6 ml of 3N HCl is added. The mixture is stirred at room temperature for 1.5 hours and is then cooled in ice. The insoluble material is collected, vacuum dried and is recrystallized from acetonitrile to give 0.4 g of 3-[4-(styrylcarbonyl)benzyloxy]-1-azabicyclo[2.2.2.]octane hydrochloride, (205°–8° C. m.p.)

EXAMPLE 22

4-anti-[4-(2-(E)-phenylethenyl)phenylmethoxy]-1-azatricyclo[3.3.1.1$^{3.7}$]decane hydrochloride 4-syn-[4-(2-(E)-phenylethenyl)phenylmethoxy]-1-azatricyclo[3.3.1.1$^{3.7}$]decane hydrochloride Step A: trimethyl-4-oxocyclohexane-1.1.3-tricarboxylate To 11.5 g (0.5 mole) sodium in 150 ml methanol is added 66 g (0.5 mole) of dimethyl malonate. This is heated to reflux and then methylacrylate (86 g, 1.0 mole) is added dropwise at a rate sufficient to maintain reflux. When the addition is completed, the reaction is heated in an oil bath at 110° C. for 2 hours. The reaction is then cooled, diluted with water (about 200 ml) and chilled overnight. The crystalline solid is filtered off, washed with ether and dried, giving crude product as the sodium salt. This is dissolved in water, acidified with concen. HCl to pH$_2$ and the white precipitate filtered and washed with water and dried to obtain trimethyl-4-oxocyclohexane-1,1,3-tricarboxylate which is used directly in the next step.

Step B: methyl 4-oxocyclohexane-1-carboxylate

A 55 g (0.2 mole) portion of trimethyl 4-oxocyclohexane-1,1,3-tricarboxylate is dissolved in 240 ml DMF and to this is added 26 g (0.445 mole) of sodium chloride and 16 ml (0.89 mole) of water, under nitrogen. This mixture is heated to reflux and maintained for 48 hours, under nitrogen. The reaction is then stripped to dryness under reduced pressure, the residue added to water and the crude product extracted into dichloromethane (3×100 ml). The combined extracts are dried over MgSO$_4$ and stopped to dryness, giving a yellow oil. This crude product is vacuum-distilled to obtain methyl 4-oxocyclohexane-1-carboxylate (b.p. 82°–108° C. at 1.0 mm Hg) which is used directly in the next step.

Step C: methyl 1,4-dioxaspiro[4.5]decane-8-carboxylate

To a solution of 8 g (0.51 mole) of methyl 4-oxocyclohexane-1-carboxylate in 50 ml of dry benzene is added 4 g (0.064 mole) of ethylene glycol and 0.10 g of p-toluenesulfonic acid and this mixture is refluxed overnight with a Dean-Stark apparatus. The cooled reaction is allowed to stand and the bottom layer (ethylene glycol) separated and the remaining benzene layer washed with aqueous sodium bicarbonate, dried over MgSO$_4$, and stripped to dryness, giving methyl 1,4-dioxaspiro[4,5]decane-8-carboxylate as a clear liquid residue. This material is used without further purification in the next step.

Step D: 1,4-dioxaspiro[4.5]decane-8-carboxamide

Sixty ml of concentrated ammonium hydroxide is added to 11.9 g (0.059 mole) of methyl 1,4-dioxaspiro[4,5]decane-8-carboxylate and stirred at room temperature overnight. The reaction is then chilled in ice and the precipitated solid filtered off, giving 4.77 g of product, m.p. 150°–6° C. A further 1.46 g product is obtained from the filtrate by stripping to dryness and recrystallizing the residue from ethyl acetate. These two portions are combined and recrystallized again from ethyl acetate to give 1,4-dioxaspiro[4,5]decane-8-carboxamide (m.p. 167°–170° C).

Step E: 6-aminomethyl-1,4-dioxaspiro[4.5]decane

To 1.4 g (0.037 mole) of lithium aluminum hydride in 100 ml dry THF is added, portionwise, 4.9 g (0.026 mole) of 1,4-dioxaspiro[4,5]decane-8-carboxamide over one-half hour. This mixture is then refluxed 2 hours, then allowed to cool to room temperature. About 5 ml water is added cautiously and then stirred 15 minutes. Dichloromethane is then added and the insolubles filtered off. The organic layer is dried over MgSO$_4$ and stripped to dryness, giving 3.48 g crude product. This material is vacuum-distilled to obtain 8-aminomethyl-1,4-dioxaspiro[4,5]decane (b.p. 84°–101° C. at 0.7 mm Hg.)

Step F: 1-azatricyclo[3.3.1.1$^{3.7}$]decane-4-one

Paraformaldehyde (2.2 g), in 320 ml 2% v/v H$_2$SO$_4$, is heated to boiling and 2.7 g (0.016 mole) of 8-aminomethyl-1,4-dioxaspiro[4,5]decane in 20 ml EtOH, is added over 4 hours. This mixture is then heated at reflux for 24 hours. The cooled reaction is washed with dichloromethane, then basified with 10N NaOH and extracted with dichloromethane. The combined extracts are dried over MgSO$_4$ and stripped to dryness, giving 1.68 g (69%) of product.

Step g. 1-azatricyclo[3.3.1.1$^{3.7}$]decane-4-ol

Sodium borohydride (0.7 g) is added to 20 ml of ice-chilled MeOH. Then 1.88 g (0.012 mole) of 1-azatricyclo [3.3.1.1$^{3.7}$]decane-4-one, in 20 ml MeOH, is added dropwise over 5 minutes. A further 0.8 g NaBH$_4$ (total 1.5 g, 0.04 mole) is added portionwise over 5 minutes. The reaction is stirred in ice one-half hour more, and then 1 hour at room temperature. The reaction is diluted with 20 ml brine, and extracted into ether. The ether is dried over MgSO$_4$ and stripped to dryness, to give 1-azatricyclo-[3.3.1.1$^{3,7}$]decane-4-ol.

Step H: 1-azatricyclo[3.3.1.1$^{3.7}$]decane-4,ol, borane complex

To a solution of 0.93 g (0.0061 mole) of 1-azatricyclo [3.3.1.1$^{3.7}$]decane-4-ol, in 60 ml of ether-THF (50/50), cooled in ice, is added 6.1 ml of 1M BH₃-THF dropwise over 3 minutes. The ice bath is removed and the reaction stirred 1 hour at room temperature. Water (35 ml) is added to the reaction and the product extracted into chloroform. The organic layer is dried over MgSO₄ and stripped to dryness, giving 0.53 g of residue (52% yield). Crude product is then dissolved in ethyl acetate and passed through silica gel in a fritted glass funnel. The ethyl acetate is stripped to obtain 1-azatricyclo[3.3.1.1³,⁷]decane-4-ol, borane complex.

Step I: anti and syn isomer of 4-[4-(2-(E)-phenylethenyl)phenyl-methoxy]-1-azatricyclo[3.3.1.1³,⁷]decane, borane complex To a suspension of 0.134 g of 60% NaH (0.0034 mole) in 10 ml DMF, under N₂, is added 1-azatricyclo[3.3.1.1³,⁷]decane-4-ol, borane complex (0.56 g, 0.0034 mole), in 10 ml DMF, dropwise over 5 minutes. This is stirred 20 minutes and then the 4-bromomethylstilbene, in 10 ml DMF, is added dropwise over 2 minutes. This is stirred at room temperature, under N₂, overnight. The reaction is then poured into 60 ml water and extracted 3 times with ether (500 ml total). The combined ether layers are washed once with brine, then dried over MgSO₄ and stripped to dryness. Crude product purified on silica gel 60 column, eluting with 5:1 hexane-:ethyl acetate. The less polar isomer is the "anti" isomer and 0.22 g of this isomer is isolated. The more polar "syn" isomer is isolated to obtain 0.11 g. These are used directly in the next step.

Step J: 4-anti-[4-(2-(E)-phenylethenyl)phenylmethoxy]-1-azatricyclo-[3.3.1.1³,⁷]decane hydrochloride Dissolved 0.22 g (0.0006 mole) of 4-anti-[4-(2-(E)-phenylethenyl)phenylmethoxy]-1-azatricyclo-[3.3.1.1³,⁷]decane borane complex in 20 ml acetone and 10 drops of 3NHCl solution is added and stirred. A white precipitate develops over an hour. The white solid is filtered and rinsed with acetone. Residual solvent is removed under high-vacuum drying at room temperature to obtain 4-anti-[4-(2-(E)-phenylethenyl)phenylmethoxy]-1-azatricyclo[3.3.1.1³,⁷]decane hydrochloride.

Step K: 4-syn-[4-(2-(E)-phenylethenyl)phenylmethoxy]-1-azatricyclo-[3.3.1.1³,⁷]decane hydrochloride Dissolved 0.11 g (0.003 mole) of 4-syn-[4-(2-(E)-phenylethenyl)-phenylmethoxy)-1-azatricyclo[3.3.1.1³,⁷]decane, borane complex in 20 ml acetone and 10 drops of 3NHCl solution is added and stirred at room temperature for 1½ hours. The solid precipitate is filtered off and rinsed with acetone and dried in a high-vacuum at room temperature to obtain 4-syn-[4-(2-(E)-phenylethenyl)phenylmethoxy]-1-azatricyclo-[3.3.1.1³,⁷]decane hydrochloride.

EXAMPLE 23

3-[4-(benzoxazol-2-yl)phenyl]methoxy-1-azabicyclo [2.2.2.]octane hydrochloride

To a solution of 1.5 g (4.84 m mole) of 3-(4-bromophenyl)methoxy-1-azabicyclo[2.2.2.]octane, borane complex in 30 ml of anhydrous THF cooled to −78° C. is added 1.94 ml (4.84 m mole) of a 2.5M hexane solution of n-butyllithium dropwise over 3 minutes. The mixture is stirred at −78° C. for 20 minutes and a solution of 0.74 g (4.84 m mole) of 2-chlorobenzoxazole in 10 ml of THF is added dropwise over 5 minutes. The cooling bath is removed and the mixture is stirred for 1 hour and is poured into 70 ml of water. The mixture is extracted with 100 ml of ether. The ether layer is washed with water and is dried over magnesium sulfate and filtered. The filtrate is diluted to the cloudy point with petroleum ether to give solid melting at 135°–8° C. This solid is suspended in 10 ml of acetone and 6 ml of 3N HCl is added. The mixture is stirred at room temperature for 1.5 hours and worked up in the usual way to give 3-[4-(benzoxazol-2-yl)phenyl]methoxy-1-azabicyclo[2.2.2]octane hydrochloride as the hydrochloride salt, 263°–5° C. m.p.)

When 2-chlorobenzoxazole in the above example is replaced by 2,5-dichlorobenzoxazole; 2-chlorobenzothiazole; 2,5-dichlorobenzothiazole and 2-chloro-5-trifluoromethylbenzoxazole then the products prepared are:

3-[4-(5-chlorobenzoxazol-2-yl)phenyl]methoxy-1-azabicyclo[2.2.2.]octane hydrochloride;

3-[4-(benzothiazol-2-yl)phenyl]methoxy-1-azabicyclo [2.2.2.]octane hydrochloride;

3-[4-(5-chlorobenzothiazol-2-yl)phenyl]methoxy-1-azabicyclo-[2.2.2.]octane hydrochloride; and 3-[4-(5-trifluoromethylbenzoxazol-2-yl)phenyl]methoxy-1-azabicyclo-[2.2.2.]octane hydrochloride.

EXAMPLE 24

Following the procedures of Examples 1–23, the representative compounds of Tables VI–IX below are prepared.

TABLE VI

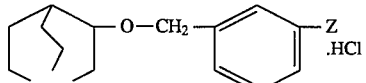

| where Z is | m.p. °C. |
|---|---|
| 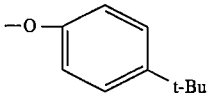 | 210–212 |
| 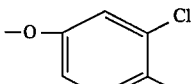 | 166–168 |
|  | 192–195(dec) |
| 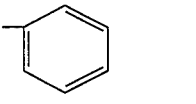 | 177–179 |
| 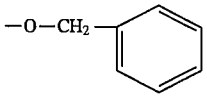 | 173–175 |
| 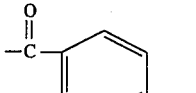 | 146–148 |

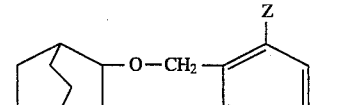

| where Z is | m.p. °C. |
|---|---|

TABLE VI-continued

[Structure: quinuclidine-O-CH₂-C₆H₄-Z · HCl]

where: Z is — m.p. °C.

| Z | m.p. °C. |
|---|---|
| phenyl | 80–83 |
| —CH₂—CH₂—phenyl | 130–133 |
| —C(=O)—phenyl | 157–159 |
| 2-benzoxazolyl | 204–207 |
| cyclohex-1-enyl | 248–250 |
| cyclohexyl | 217–219 |
| 4,4-dimethylcyclohex-1-enyl | 250–252 |
| 3,3,5,5-tetramethylcyclohex-1-enyl | 196–198 |
| 3,3,5,5-tetramethylcyclohex-1-enyl (isomer) | 150–152 |
| —C(=O)-(5-methylthien-2-yl) | 174–177 |
| pyridin-2-yl | — |
| —CH=CH-(2,4-dimethylphenyl) | 178–180 |
| —CH=CH-(3,4-dichlorophenyl) | 210–213 |
| —CH=CH-(4-fluorophenyl) | 247–251 |
| —CH=CH-(4-trifluoromethylphenyl) | — |
| —C(=CH₂)-phenyl | 145–149(dec) |
| —C(=CH₂)-(2-chlorophenyl) | 162–165 |
| —CH₂—C(=CH₂)-phenyl | — |
| —C(OH)(Me)-phenyl | 177–179 |
| —C(=O)-phenyl | 140–143 |
| —C(=O)-(4-chlorophenyl) | 186–188 |
| —C(=O)-(3-chlorophenyl) | 172–174 |
| —C(=O)-(3-fluorophenyl) | 168–170 |
| —C(=O)-(2-fluorophenyl) | 156–158 |

TABLE VI-continued

| Structure | mp (°C) |
|---|---|
| 4-F-C6H4-C(=O)- | 173–175 |
| 4-MeO-C6H4-C(=O)- | 188–191 |
| 4-Me-C6H4-C(=O)- | 175–180 |
| 4-t-Bu-C6H4-C(=O)- | 166–168 |
| -CH2-C(=O)-C6H5 | — |
| Me2C(-)-C(=O)-C6H5 | 177–179 |
| O=C(Me)-N(Me)-C6H5 | 148–150(dec) |
| -O-C6H5 | 158–160 |
| -O-CH2-C6H5 | 156–158 |
| -S-C6H5 | — |
| -S-CH2-C6H5 | — |
| -SO2-C6H4-4-Me | 171–174 |
| indenyl | 200–203 |
| 6-OMe-indenyl | 198–201(dec) |
| 5-OMe-indenyl | 166–169 |
| 1,1-dimethyl-indenyl | 170–172 |
| chromone | 252–255 |
| 3,7-dimethyl-dihydronaphthyl | 178–182(dec) |
| dihydronaphthyl | 187–190 |
| naphthyl | 222–224 |
| naphthyl (isomer) | — |
| benzocycloheptenyl | 184–187(dec) |
| 4-methyl-dihydrobenzothiophenyl | 200–203(dec) |
| 2,4-dimethyl-benzoxazolyl | 263–265 |

TABLE VI-continued
| Structure | mp (°C) |
|---|---|
| 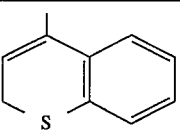 | 140(dec) |
| 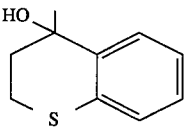 | 200–203 |
| 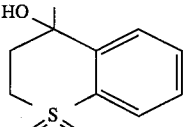 | 120 |
| 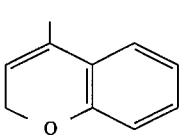 | 178–181 |
| 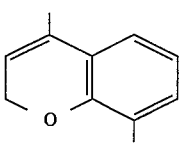 | 243–245 |
| 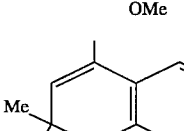 | 168–171 |
| 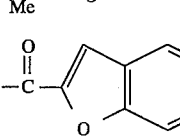 | 210–213 |
| 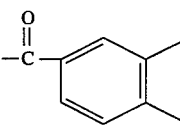 | 165–167 |
| 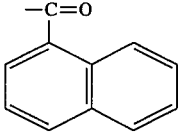 | 183–186 |
| 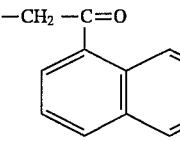 | |
| 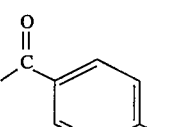 | 182–184 |
TABLE VI-continued
| Structure | mp (°C) |
|---|---|
| 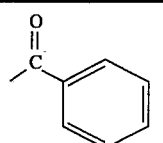 | 174–176 |
| 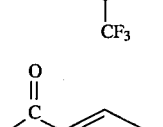 | 174–176(dec) 2 HCl |
| 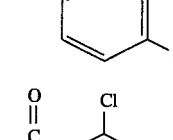 | 148–150 |
| 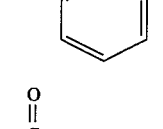 | 203–206 |
| 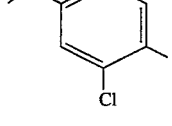 | 194–197 |
| 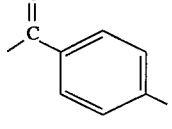 | 217–219 |
| 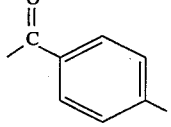 | 144–147 |
| 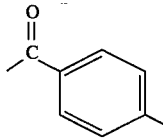 | 205–208 |
| 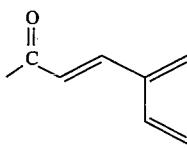 | 145–148 |
| 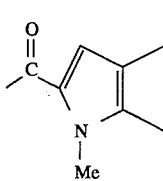 | 230–232 |

TABLE VI-continued

| Structure | mp (°C) |
|---|---|
| 3-acetylpyridine | 197–200, 2 HCl |
| 6-chloro-3-acetylpyridine | 177–180(dec) |
| 5-chloro-2-acetylthiophene | 241–243 |
| 4-(methylthio)benzoyl | 159–162 |
| 2-furoyl | 147–150 |
| piperonyloyl (1,3-benzodioxol-5-yl carbonyl) | 192–200 |
| 2-methyl-oxazolo[4,5-b]pyridine | 235–238(dec), 2 HCl |
| 2-phenyl-4-methylthiazole | 233–235 |
| 2-methylbenzofuran | 250–252 |
| 1,2-dimethylindole | 202–204 |
| 1,2-dimethylbenzimidazole | 160(dec), 2 HCl |
| 2-methylbenzothiophene | 255–258 |
| 5-chloro-2-methylbenzoxazole | 243–246 |
| 2-methylbenzoxazole | 263–265 |
| 2-methylbenzothiazole | 270–272 |
| 2-methylquinoline | 173–176(dec), 2 HCl |
| (E)-3-(2-hydroxyphenyl)propenoyl (coumarinyl) | 258–260 |
| 2-methyl-N-methylquinazolin-4(3H)-one type | 233–235(dec), 2 HCl |
| 6-methoxy-2-methylnaphthalene | 258–260 |
| 9-methylphenanthrene | 195–197 |
| 5-methylacenaphthylene | 214–217 |
| 5-hydroxyacenaphthylene | — |
| phenothiazine N-methyl | — |

TABLE VII

[Structure: quinuclidine-O-CH₂-phenyl-Z .HCl, with Me substituent]

where Z is | m.p. °C.
---|---
[4-chlorobenzoyl: -C(=O)-C₆H₄-Cl] | 211–213
[benzoxazol-2-yl] | 285–290

TABLE VIII

| Structure | m.p. °C. |
|---|---|
| [quinuclidine-O-CH₂-naphthyl-benzoxazole] .HCl | 268–270 |
| [quinuclidine-O-CH₂-thienyl-benzoxazole] .HCl | 259–261 |
| [quinuclidine-O-CH₂-benzoxazole-phenyl-Cl] .HCl | 275–277 |

TABLE IX

[Structure: Z-phenyl-CH₂-O-adamantyl-N .HCl]

| where: Z is | | m.p. °C. |
|---|---|---|
| [benzoxazol-2-yl] | 4-syn | 267–270(dec) |
| [benzoxazol-2-yl] | 4-anti | 335(dec) |
| [4-chlorobenzoyl] | 4-syn | 237–239 |

TABLE IX-continued

[Structure: Z-phenyl-CH₂-O-adamantyl-N .HCl]

| where: Z is | | m.p. °C. |
|---|---|---|
| [4-chlorobenzoyl] | 4-anti | 279–281 |
| [styryl/propenyl-phenyl] | 4-syn | 323–326 |
| [styryl/propenyl-phenyl] | 4-anti | 319–321(dec) |

EXAMPLE 25

3-[4-(1,3-benzodioxole-5-yl) benzyloxy]-1-azabicyclo[2,2,2]octane hydrochloride

Step A: 4-methyl-3', 4'-methylenedioxy-1,1-biphenyl

To a solution of 10g (58.4 m mole) of 4-bromotoluene in 75 ml of anhydrous THF cooled to −78° C. is added 23.4 ml (58.4 m mole) of a 2.5M hexane solution of n-butyllithium dropwise over 5 minutes. The mixture is stirred at −70° C. for 10 minutes and 58.4 ml (58.4 m mole) of 1M zinc chloride is added dropwise over 5 minutes. The cooling bath is removed and the mixture stirred for 1.5 hours warming to room temperature. This mixture is then added dropwise over 5 minutes to a mixture of 9 g (45 m mole) of 4-bromo-1, 2(methylenedioxy)benzene and 0.67 g (0.58 m mole) of tetrakis(triphenylphosphine) palladium (0) in 100 ml of THF. The mixture is heated under reflux for 10 hours. The mixture is cooled and poured into 100 ml of water and extracted with 200 ml of ether. The ether layer is washed with water and dried over magnesium sulfate and then filtered. The filtrate is evaporated and the residue recrystallized from hexane to give 4-methyl-3', 4'-methylenedioxy-1,1-biphenyl (m.p. 57°–60°).

Step B 4-bromomethyl-3', 4'-methylenedioxy-1,1-biphenyl

A mixture of 4.6 g (21.67 m moles) of 4-methyl-3', 4'-methylenedioxy-1,1-biphenyl and 5.0 g (28 m moles) of N-bromosuccinimide in 70 ml of carbon tetrachloride containing 0.1 g of benzoyl perioxide is heated under reflux for 2.5 hours. The mixture is filtered and the filtrate evaporated. The residue is recrystallized from hexane to afford (m.p. 78°–81°).

Step C. 3-[4-(1,3-benzodioxol-5-yl) benzyloxy]-1-azabicyclo[2.2.2]octane hydrochloride To a suspension of 0.14 g (3.44 m mole) of 60% sodium hydride in 20 ml of anhydrous DMF is added a solution of 0.48 g (3.44 m mole) of 3-quinuclidinol borane complex in 10 ml of DMF dropwise over 3 minutes. The mixture is stirred at room temperature for 15 minutes and a solution of 1.0 g (3.44 m moles) of 4-bromomethyl-3', 4'-methylenedioxy-1,1-biphenyl in 10 ml of DMF was added dropwise over 5 minutes. The mixture is stirred at room temperature for 2 hours and poured into 75 ml of water and extracted with 150 ml of ether. The ether is washed with water, dried over magnesium sulfate and filtered. The filtrate is evaporated and the residue purified by flash chromatography using 4:1 hexane:ethyl acetate to give a solid with 100°–3° mp. This solid is suspended in 10 ml of acetone and ethanolic hydrochloric acid is added to pH1. The mixture is stirred at room temperature for 15 minutes and then diluted with ether to precipitate 3-[4-(1,3-benzodioxol-5-yl) benzyloxy]-1-azabicyclo[2.2.2]octane hydrochloride (m.p. 195°–8°).

Analysis Calc for $C_{21}H_{24}ClNO_3$ C:67.46; H:6.47; N:3.75 Found: C:67.08; H:6.53; N:3.53

EXAMPLE 26

Following the procedure of Example 25 the following compounds may be prepared.

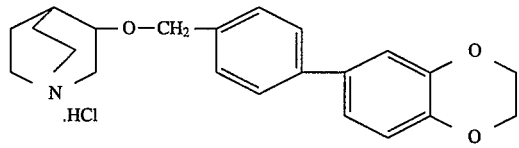

3-[4-(1,4-benzodioxan-6-yl)benzyloxy]-1-azabicyclo [2.2.2]octane hydroxhloride (m.p. 248°–250° C.)

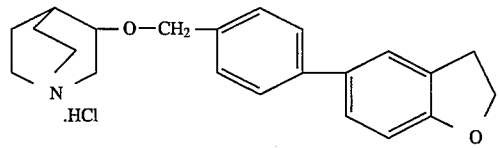

3-[4-(2,3-dihydrobenzofuran-5-yl)benzyloxy-1-azabicyclo [2.2.2]octane hydrochloride (m.p. 204°–207 ° C.)

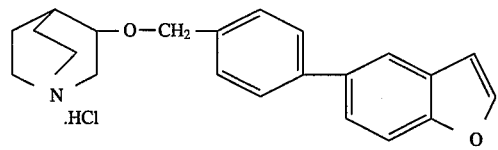

3-[4-(benzofuran-5-yl)benzyloxy]-1-azabicyclo [2.2.2] octane hydrochloride (m.p. 220°–222 ° C.)

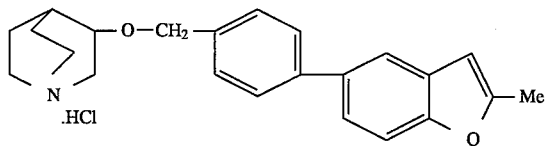

3-[4-(2-methylbenzofuran-5-yl)-1-azabicyclo[2.2.2]octane hydrochloride (m.p. 204°–207 ° C)

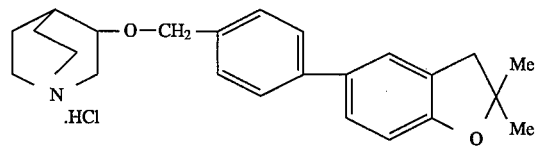

3-[4-(2,2-dimethyl-2,3-dihydrobenzofuran-5-yl)benzyloxy]-1-azabicyclo[2.2.2]octane hydrochloride (m.p. 237°–239 ° C.)

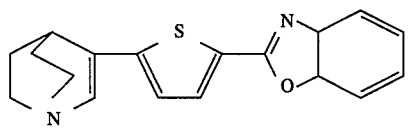

3-[5-(thien-2-yl)benzoxazol-2-yl]-1-azabicyclo[2.2.2]oct-2-ene

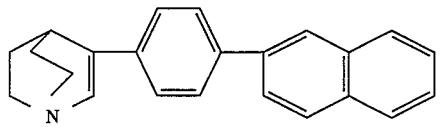

3-[(4-phenyl)naphth-2-yl]-1-azabicyclo[2.2.2]oct-2-ene

EXAMPLE 27

Following the procedures in the foregoing examples, the following representative compounds may be prepared.

3-[4-(3-methoxyphenyl)phenyl]methoxy-1-azabicyclo [2.2.2]octane hydrochloride (m.p. 160°–163° C.)

3-hydroxy-3-[4-(3-methoxyphenyl)phenyl]-1-azabicyclo [2.2.2]octane hydrochloride (m.p. 215°–217° C.)

3-[4-(2-(E)-phenylethenyl)phenoxy]-1-azabicyclo[2.2.2] octane hydrochloride (m.p. 255°–258° C.)

4-((1-azabicyclo[2.2.2] octane-3-yl)oxy)phenyl-(4-chlorophenyl)methanone hydrochloride (m.p. 178°–181° C.)

3-[4-(3-methoxyphenyl)phenoxy]-1-azabicyclo[2.2.2]octane hydrochloride (m.p. 209°–211° C.)

3-[4-(benzoxazol-2-yl)phenyl]-3-hydroxy-2-methyl-1-azabicyclo[2.2.2]octane (m.p. 266°–268° C.)

3-[4-(benzoxazol-2-yl)phenyl]-3-hydroxy-1-azabicyclo [2.2.2] octane hydrochloride (m.p. 293°–295° C. dec.)

3-[4-(benzoxazol-2-yl)phenoxymethyl]-1-azabicyclo [2.2.2]octane dihydrochloride (m.p. 287°–290° C. dec.)

3-[4-(benzoxazol-2-yl)phenyl]-2-methyl-1-azabicyclo [2.2.2]oct-2-ene hydrochloride (m.p. 280° C. dec.)

3-[4-(benxoxazol-2-yl)phenyl]-2-methyl-1-azabicyclo [2.2.2]octane hydrochloride (m.p. 303°–306° C. dec.)

3-[4-(benzoxazol-2-yl)phenyl]-1-azabicyclo[2.2.2]oct-2-ene hydrochloride (m.p. 286° C. dec.)

3-[4-(benzoxazol-2-yl)phenyl]-1-azabicyclo[2.2.2]octane hydrochloride (m.p. 285° C. dec.)

3-[4-(benzoxazol-2-yl)phenoxy]-1-azabicyclo[2.2.2]octane dihydrochloride (m.p. 270°–273° C.)

3-[4-(2,3-dihydro-1,4-benzodioxin-6-yl)phenoxy]-1-azabicyclo[2.2.2]octane hydrochloride (m.p. 298°–300° C.)

3-[4-(2,3-dihydro-1,4-benzodioxin-6-yl)phenyl]-3-hydroxy-1-azabicyclo-[2.2.2]octane hydrochloride (m.p. 234°–236° C.)

3-[4-(1,4-benzodioxin-2-yl)phenoxy-1-azabicyclo[2.2.2] octane hydrochloride (m.p. 220°–222° C.)

3-[4-(2,3-dihydro-1,4-benzodioxin-6-yl)phenyl]methoxy-1-azabicyclo[2.2.2]octane hydrochloride (m.p. 248°–250° C.)

3-[4-(1-methylindole-2-yl)phenoxy]-1-azabicyclo[2.2.2] octane hydrochloride (m.p. 273°–275° C.)

3-[4-(benzofuran-5-yl) phenyl]methoxy-1-azabicyclo [2.2.2]octane hydrochloride (m.p. 220°–222° C.)

3-[4-(benzofuran-5-yl)]phenoxy-1-azabicyclo[2.2.2] octane hydrochloride (m.p. 301°–303° C.)

3-[5-(2,3-dihydro-1,4-benzodioxin-6-yl)oxazol-2-yl] methoxy-1-azabicyclo[2.2.2]octane dihydrochloride (m.p. 138°–140° C.)

Various tests in animals have been carried out to show the ability of the compounds of the present invention to exhibit pharmacological responses that can be correlated with activity in humans. These tests involve such factors as the effect of the compounds of Formula I to inhibit squalene synthesis. It has been found that compounds within the scope of this invention when tested using the following procedures show a marked activity for the inhibition of squalene syntase and hence are believed to be useful in the treatment of. cholesterol-related disorders.

Squalene Syntase Inhibition Assay

The squalene syntase assay used is a modification of the procedures described by Popjak (1969) and Poulter et al. (1989):

Popjak, G. Enzymes of sterol biosynthesis in liver and intermediates of sterol biosynthesis. Meth. Enzymol. 15: 393–454, 1969.

Poulter, C. D., Capson, T. L., Thompson, M. D. and Bard R. S. Squalene syntase. Inhibition by ammonium analogues of carbocationic intermediates in the conversion of presqualene diphosphate to squalene. J. Am. Chem. Soc. 111: 3734–3739, 1989.

I. Animal Source and Tissue Preparation:

Four male Sprague-Dawley rats weighing 100–120 gms are fed a low cholesterol rodent diet (#5012) obtained from Purina Mills, Inc. in Richmond, Ind.; and housed under reverse-light. Water is given ad lib. Rats are lightly anesthetized with ether and then decapitated. Livers are removed and enzymes are separated by the method described below.

II. Materials:
Chemicals:

All Chemicals are "A.C.S." in purity or better unless noted;

AquaSol®-2 scintillation fluid (NEF-952) (Du Pont/NEN Research Products, Boston, Mass.);

Anhydrous $MgCl_2$ (M-8266), B-NADPH tetrasodium salt, reduced form (N-1630), Bovine serum albumin (A-6003), Cholesterol (C-8503);

Squalene (S-3626), (Sigma Chemical Co., St. Louis, Mo.);

Bio-Rad protein assay dye concentrate (Bio-Rad Laboratories, Richmond, Calif.);

Denatured ethanol, DMSO, HCl (1N), KOH, methanol, NaOH (0.1N,1N), petroleum ether (M-280 grade), potassium phosphate dibasic, 2-propanol (Fisher Scientific, Pittsburgh, Pa);

Zero grade nitrogen gas mixture (certified analysis) (Woodland Oxygen & Supply Co., Philadelphia, Pa).

Radiochemicals:

[1-$^3$H(N)]-FPP, triammonium salt (NET-1042), (Du Pont/NEN, Boston, Mass.);

[4,8,12,13,17,21-$^3$H]-Squalene (NET-645) (Du Pont/NEN);

Non-radiolabeled FPP is prepared in-house. The solid FPP is aliquoted and stored at −80° C. FPP is dissolved in 70% ethanol/30% 0.25M $NH_4HCO_3$ at the concentration of 10 mM and the solution is aliquoted (200 µl each) and stored at −80° C.

III. Preparation of Assay Substances:
A) Test Solutions:

Test solutions are prepared fresh in 100% DMSO or $dH_2O$. Subsequent dilutions are made in the same solvent. Compounds are tested initially at 1 or 10 µl (final concentrations).

B) Assay Buffer:

Potassium Phosphate (50 mM, 8.71 g/l) pH 7.5 stock buffer is prepared and stored at 4° C. until use. Anhydrous $MgCl_2$ is added to the phosphate buffer on the day of assay for a final concentration of 10mM (95 mg/100 ml). The buffer is flushed with N2 before use.

C) Substrate:

Non-radiolabeled FPP is diluted to 50 µl (100 µl 10 mM cold FPP +19.9 ml phosphate buffer). Then, 14 µl (20×10$^6$ dpm) of $^3$H-FPP (0.5 mCi/ml, 0.011 mg/ml) is added. 200 µl of this mixture is added per assay tube for a final reaction concentration of 10 µM FPP (~200,000 dpm/assay tube).

D) β-NADPH Solution:

37.5 mg of β-NADPH is added to 9 ml assay buffer for a 5 mM concentration of β-NADPH. The mixture is vortexed and 100 µl of this solution is added to each tube for a final assay concentration of 0.5 mM β-NADPH.

E) KOH in Ethanol:

75 gm of KOH is dissolved in 500 ml of denatured ethanol for a 15% solution and stored at 0° C. until use. 1 ml of this solution is added per tube to terminate the reaction.

IV. Experimental Procedure:
A) Enzyme Preparation:

Immediately following decapitation, livers are removed one at a time from four rats. The livers are combined and weighed in a tared beaker. Assay buffer is added equal to three times the liver weight. The liver is first homogenized with a blender for thirty seconds, and then by a motor driven teflon pestle at a speed of 2.5. During homogenization, the liver is kept on ice. When the liver is fully homogenized, the homogenate is centrifuged at 10,000 g for 30 min at 4° C. in 50 ml capacity centrifuge tubes. The mitochondrial pellet is discarded and the supernatant is filtered through a layer of gauze moistened with a little buffer. This supernatant is recentrifuged at 105,000 g for one hour at 0° C. in an ultracentrifuge in 25 ml capacity ultracentrifuge tubes.

Following centrifugation, the supernatant is removed and discarded. The sediment pellet consists of 2 layers: a transparent inner layer of glycogen, surrounded by an opaque brown layer of microsomes. The brown outer microsomal layer is carefully removed with a spatula and placed in a beaker on ice. Assay buffer is added in an amount equal to one half the original homogenate volume, and this mixture is poured into ultracentrifuge tubes. These tubes are recentrifuged at 105,000 g for 1 hour at 4° C.

After this centrifugation is complete, the supernatant is again removed and discarded. Fresh assay buffer is added to the combined pellets to achieve a volume equal to one tenth of the original homogenate volume. The microsomal fraction is then rehomogenized on a motor driven teflon pestle at a speed of 2.5 to partially solubilize and make a uniform suspension of the microsomes. The enzyme (~20 ml, ~40 mg protein/ml) is aliquoted (200 µl) into eppendorf plastic tubes, capped and stored at −80° C. until use.

B) Assay Procedure

To begin the assay, 20 µl of the compound of this invention or vehicle solution is added to each 16×150 screw-cap culture tube on ice. Then 580 µl of $N_2$ flushed assay buffer is pipetted into each tube. 100 µl of cofactor is next added to each tube, followed by 100 µl of a dilution of microsomal enzyme (approximately 80 ug protein). The tubes are preincubated for 10 minutes at 37° C., and 200 µl of the $^3$H-FPP (200,000 dpm, 10 µM final conc.) is added to each tube at two second intervals. The tubes are then incubated for exactly 10 minutes, shaking at 150 oscillations per minute. After the 10 minute incubation, the reaction is stopped by the addition of 1 ml of 15% KOH in ethanol, and the tubes are incubated for 30 minutes in a 65° C. water bath for saponification of lipids and solubilization of proteins. The tubes are cooled on ice for five minutes. The samples are next extracted with 5 ml of petroleum ether by shaking for 10 minutes at low speed on a metabolic shaker. Each lower aqueous layer is frozen in a dry ice/alcohol bath (2-propanol/ methanol, 1:1), and each organic layer is poured into another set of 16×150 screw-top culture tubes containing 2 ml of deionized water. Each ether layer is washed by vortexing each tube for 5 seconds. The aqueous layers are again frozen in the dry ice/alcohol bath, and the ether is poured into scintillation vials. 10 ml of AquaSol® is next added to each vial, and the vials are counted for 5 minutes in a scintillation counter. Percent inhibitions are calculated from the counts obtained.

V. Statistical Consideration

The samples are counted as dpm using a Beckman Scintillation counter (Model LS-9000). Percent inhibition is calculated using a Lotus 1-2-3 program. The $IC_{50}$ values are calculated using a linear regression program of Tallarida and Murray (1987). Tallarida, R. J. and Murray, R. B. Manual of pharmacologic calculations with computer programs. Springer-Verlag, 1987.

In view of the results obtained by the foregoing assay procedure, compounds within the scope of Formula I inhibit squalene syntase enzyme activity and are useful as hypocholesterolemic or hypolipidemic agents by virtue of their ability to inhibit the biosynthesis of cholesterol. Having such ability, the compounds are incorporated into pharmaceutically acceptable carriers and administered to a patient in need of such cholesterol biosynthesis inhibition. These pharmaceutical formulations contain at least one compound according to this invention.

In theory, treatment with a combination of an HMG-CoA reductase inhibitor and a squalene syntase inhibitor could have a synergistic effect on inhibiting cholesterol biosynthesis. Inhibiting the squalene syntase enzyme and the HMG-CoA reductase enzyme at the same time would most closely resemble the physiological conditions of cholesterol homeostasis. A squalene syntase inhibitor could keep cellular concentrations of farnesyl diphosphate high enough for the synthesis of the small amounts of dolichol, ubiquinone, and the farnesylated proteins required by the cell. This would maintain some feedback regulation of the HMG-CoA reductase enzyme and allow smaller amounts of the HMG-CoA reductase inhibitor to be used.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelially including transdermal, opthalmic, sublingual and buccal; topically including opthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent of dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carders, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from about 0.1 to about 100 mg/kg/dy, and preferably from about 10 mg to about 1000 mg day, or from about 0.1 mg to about 50 mg/kg of body weight per day and preferably from about 0.1 to about 20 mg/kg of body weight per day and may be administered in several different dosage units. Higher dosages on the order of about 2× to about 4× are required for oral administration.

We claim:

1. A compound of the formula

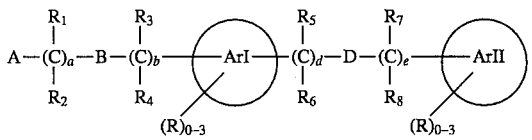

where:

Ar I is a substituted or unsubstituted phenylene or naphthylene and where the substituents may be located at any appropriate position of the ring system and are described by R;

Ar II is a substituted or unsubstituted benzoxazolyl and where the substituents may be located at any appropriate position of the ring system and are described by R;

A is

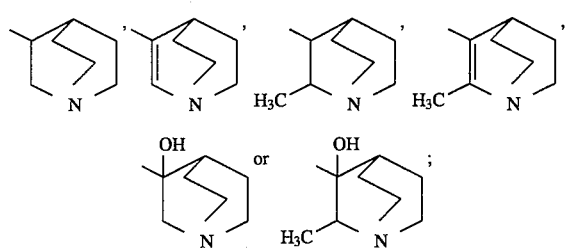

B is CR'R', O or a bond;

D is CR'R', R'C=CR', C≡C, C=CHR' or a bond;

$R_1$, $R_2$, $R_3$, $R_4$, $R_5$, $R_6$, $R_7$ and $R_8$ are independently hydrogen or $(CH_2)_x$—X where x is 0–5 and X is hydrogen, alkyl, alkenyl, aralkyl, hydroxy, alkoxy, aralkoxy, aryloxy, acyloxy, aryl, halo, amino, mono- and di-alkylamino or acylamino;

R' is hydrogen, alkyl or aralkyl;

R is hydrogen, alkyl, aralkyl, hydroxy, alkoxy, aralkoxy, acyloxy, halo, haloalkyl, amino, mono- and di-amino or acylamino; and a, b, d and e are 0–4; or a pharmaceutically acceptable salt thereof.

2. A compound according to claim 1 where:

Ar I is phenylene or naphthylene;

Ar II is benzoxazol-2-yl;

A is

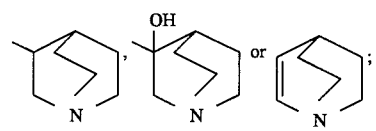

B is CR'R', O or a bond; D is CR'R' R'C=CR', C≡C, C=CHR or a bond;

$R_1$, $R_2$, $R_3$, $R_4$, $R_5$, $R_6$, $R_7$ and $R_8$ are independently hydrogen or $(CH_2)_x$—X where x is 0–5 and X is hydrogen, alkyl, hydroxy, alkoxy, aryloxy, aralkoxy or aryl;

R' is hydrogen, alkyl or aralkyl;

R is hydrogen, alkyl, hydroxy, alkoxy, halo or haloalkyl; and a, b, d and e are 0–4.

3. A compound according to claim 2 where:

Ar I is phenylene or naphthylene;

Ar II is benzoxazol-2-yl;

A is

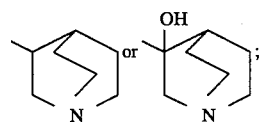

B is CR'R', O or a bond;

D is CR'R', C≡C, C=CHR' or a bond;

$R_1$, $R_2$, $R_3$, $R_4$, $R_5$, $R_6$, $R_7$ and $R_8$ are independently hydrogen or $(CH_2)_x$—X where x is 0–3 and X is hydrogen, alkyl, hydroxy or phenyl;

R' is hydrogen or loweralkyl;

R is hydrogen, loweralkyl, hydroxy, loweralkoxy, halo or trifluoromethyl; and a, b, d and e are 0–4.

4. A compound according to claim 3 where:

Ar I is phenylene.

5. A compound according to claim 1 of the formula;

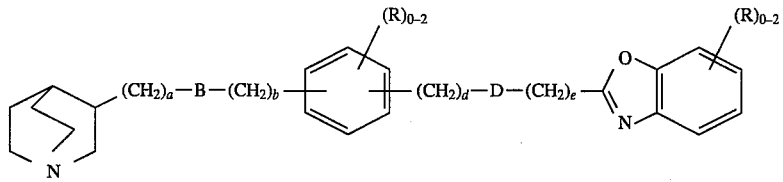

where
 B is CR'R', O or a bond;
 D is CR'R', R'C=CR', C≡C, C=CHR' or a bond;
 R is hydrogen, loweralkyl, hydroxy, loweralkoxy, halo or trifluoromethyl; and
 a, b, d and e are 0–4.

6. A compound according to claim 1 of the formula;

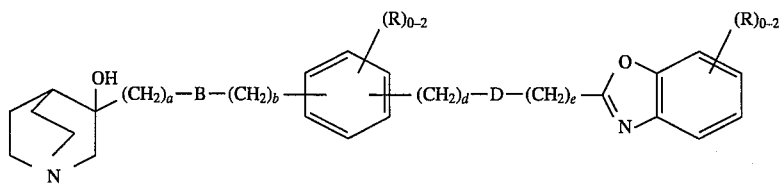

where
 B is CR'R', O or a bond;
 D is CR'R', R'C=CR', C≡C, C=CHR' or a bond;
 R is hydrogen, loweralkyl, hydroxy, loweralkoxy, halo or trifluoromethyl; and
 a, b, d and e are 0–4.

7. A method of lowering or maintaining reduced cholesterol levels in a patient requiring such treatment which comprises administering to such patient a squalene synthase inhibitor effective amount of a compound of the formula according to claim 1.

8. A method for inhibiting cholesterol biosynthesis which comprises administering to a patient in need of such inhibition a squalene synthase inhibiting effective amount of a compound according to claim 1.

9. A method according to claim 8 where the compound of claim 1 is a hypocholesterolemic or hypolipidemic agent.

10. A method according to claim 9 for treating atherosclerosis.

11. A pharmaceutical composition comprising a squalene synthase inhibitor effective amount of a compound according to claim 1 in admixture with a pharmaceutical carrier.

* * * * *